(12) United States Patent
Hakii et al.

(10) Patent No.: US 7,745,124 B2
(45) Date of Patent: Jun. 29, 2010

(54) HYBRIDIZATION METHOD

(75) Inventors: Chikako Hakii, Yokohama (JP);
Mitsugu Usui, Yokohama (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 630 days.

(21) Appl. No.: 11/579,063

(22) PCT Filed: Apr. 28, 2005

(86) PCT No.: PCT/JP2005/008248

§ 371 (c)(1),
(2), (4) Date: Oct. 27, 2006

(87) PCT Pub. No.: WO2005/106031

PCT Pub. Date: Nov. 10, 2005

(65) Prior Publication Data

US 2008/0248963 A1    Oct. 9, 2008

(30) Foreign Application Priority Data

Apr. 28, 2004 (JP) ............................. 2004-133870

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................. 435/6; 536/23.1, 24.3
See application file for complete search history.

(56) References Cited

U.S. PATENT DOCUMENTS

| | | | |
|---|---|---|---|
| 5,437,977 A * | 8/1995 | Segev | 435/6 |
| 5,484,904 A | 1/1996 | Nilsen et al. | |
| 6,255,051 B1 | 7/2001 | Hammond et al. | |
| 6,261,846 B1 * | 7/2001 | Usui | 436/94 |
| 7,060,814 B2 * | 6/2006 | Usui et al. | 536/24.3 |
| 7,122,310 B2 * | 10/2006 | Usui et al. | 435/6 |
| 7,393,636 B2 * | 7/2008 | Usui et al. | 435/6 |
| 2002/0155477 A1 * | 10/2002 | Ito | 435/6 |
| 2003/0175689 A1 * | 9/2003 | Usui et al. | 435/5 |
| 2003/0198962 A1 | 10/2003 | Chung et al. | |

FOREIGN PATENT DOCUMENTS

| | | |
|---|---|---|
| EP | 1 188 840 | 3/2002 |
| EP | 1 188 841 | 3/2002 |
| EP | 1 431 386 | 6/2004 |
| JP | 3267576 | 1/2002 |
| JP | 3310662 | 5/2002 |
| JP | 2002-214192 | 7/2002 |
| JP | 2002-355081 | 12/2002 |
| WO | 92/20702 | 11/1992 |
| WO | WO01/75157 * | 10/2001 |
| WO | 02/09868 A2 | 2/2002 |
| WO | 02/09868 A3 | 2/2002 |
| WO | 02/31192 | 4/2002 |
| WO | WO02/31192 * | 4/2002 |
| WO | 03/029441 | 4/2003 |
| WO | WO03/040367 * | 5/2003 |
| WO | 03/072817 A2 | 9/2003 |
| WO | 2003/072817 A3 | 9/2003 |

OTHER PUBLICATIONS

Matthews et al. Review : Analytical Strategies for the use of DNA probes. Analytical Biochemistry 169: 1-25 (1988).*
Saiki et al. Genetic analysis of amplified DNA with immobilized sequence-specific oligonucleotide probes. PNAS 86 : 6230-6234(1989).*
A. Marshall et al., "DNA Chips: An Array of Possibilities", Nature Biotechnology, vol. 16, pp. 27-31, Jan. 1998.
A. A. Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, vol. 54, pp. 3607-3630, 1998.
A. A. Koshkin et al.,"LNA (Locked Nucleic Acid): An RNA Mimic Forming Exceedingly Stable LNA:LNA Duplexes", J. Am. Chem. Soc., vol. 120, pp. 13252-13253, 1998.
C. Wahlestedt et al., "Potent and Nontoxic Antisense Oligonucleotides Containing Locked Nucleic Acids", PNAS, vol. 97, pp. 5633-5638, 2000.
H. C. Birnboim et al., "A Rapid Alkaline Extraction Procedure for Screening Recombinant Plasmid", Nucleic Acids Research, vol. 7, No. 6, pp. 1513-1523, 1979.
Patent Cooperation Treaty (PCT) International Preliminary Report on Patentability, issued Nov. 14, 2006 in International Application No. PCT/JP2005/008248.

* cited by examiner

*Primary Examiner*—Ethan Whisenant
(74) *Attorney, Agent, or Firm*—Wenderoth, Lind & Ponack, L.L.P.

(57) ABSTRACT

A hybridization method is provided in which an efficient hybridization reaction can be carried out. Further, there are provided, using this hybridization method, a method for detecting a target gene with high sensitivity and a signal amplifying method for markedly improving the detection sensitivity of the target gene. There is provided a hybridization method comprising the use of oligonucleotides in a reaction solution, the method comprising forming partially a reaction temperature region in the reaction solution and performing a hybridization reaction in the reaction temperature region.

32 Claims, 12 Drawing Sheets

(a)

(b)

(c)

(d)

(e)

(f)

(a)

(b)

(c)

(a)

(b)

(c)

(a) At 45°C of the bottom part for 1 hour (b) At 45°C of the bottom part and 20°C of the top part for 1 hour

HYBRIDIZATION METHOD

This application is a U.S. national stage of International Application No. PCT/JP2005/008248 filed Apr. 28, 2005.

TECHNICAL FIELD

The present invention relates to a hybridization method wherein, in hybridization reaction using oligonucleotides, a reaction temperature region is partially formed in a reaction solution, and a hybridization reaction is carried out in the reaction temperature region to effectively form a hybrid. The present invention also relates to a method of detecting a gene using the hybridization method. The present invention further relates to a signal amplifying method using the hybridization method, wherein there is improved the detection sensitivity of a target gene bonded to a gene detecting device, such as a DNA chip or a DNA microarray (see Non-Patent Document 1 and the like. In the present specification, a DNA chip and a DNA microarray are referred collectively to as a "DNA microarray"), a microplate and a magnetic particle and the like.

BACKGROUND ART

A reaction device for detecting genes, e.g. a microplate, a DNA microarray, a magnetic particle and the like (hereinafter referred to as a "reaction platform") are available at a low price and can easily control a reaction temperature uniformly, and a special machine is not necessary for using them. Therefore, many kinds of gene diagnostic kits using a luminous enzyme or a coloring enzyme are commercially available.

At present, temperature control of these reaction platforms is performed using a usual machine called a thermostatic bath. Especially, in detecting genes, a target gene or a gene amplified by a PCR method or the like is labeled with an enzyme or the like, and the detecting reaction is usually performed as a normal biochemical reaction at a uniform reaction temperature using the thermostatic bath.

On the other hand, the present inventors have proposed a novel isothermal nucleic acid amplification method using no enzyme (a method for forming a probe self-assembly substance) (see Patent Documents 1 to 4). FIGS. 1 to 3 are schematic explanatory drawings showing the method described in Patent Document 1. For example, a method described in Patent Document 1 uses a pair of oligonucleotide probes 18 (the probe is called a "Honey Comb Probe", and hereinafter referred to as a "HCP") as shown in FIG. 1. The probes consist of a first HCP (a X region, a Y region and a Z region) and a second HCP (a Z' region, a Y' region and a X' region). The three regions of each HCP are complementary to each other in their base sequences. The base sequences of the HCPs are designed such that they are hybridized through a couple of regions corresponding to each other when reacting them to each other (FIG. 2). By this design, when reacting plural pairs of HCPs, as shown in FIG. 9, they are hybridized with each other depending on the reaction temperature to form a self-assembly substance of probes 20 (arrows of FIG. 9) (FIG. 3). In the present specification, the method for forming a self-assembly substance by the self-assembly reaction using these oligonucleotide probes (a probe alternation link self-assembly reaction) is referred to as a PALSAR method.

Also the present inventors have found that the detection sensitivity of a target gene can be improved by using the PALSAR method (Patent Document 5). In FIG. 4, there is shown an example of a signal amplifying method with a microplate using the PALSAR method. As shown in FIG. 4(a), a capture probe 14 (a probe for capturing a gene) for a target gene 12 is bonded to the reaction device such as a microplate 10. Next, as shown in FIG. 4(b), the target gene 12 is captured. After that, as shown in FIG. 4(c), there is added oligonucleotide DNA 16 having complementary regions to a HCP and the target gene (a joint probe in Patent Document 5). In the present invention, the probe having complementary sequence to the target gene to be detected and a nucleic acid (probe) forming a self-assembly substance is referred to as an assist probe. Further, as shown in FIG. 4(e), plural pairs of HCPs 18 are added to form a self-assembly substance 20 by the self-assembly reaction, thereby the signal amplification being realized.

Patent Document 1: JP 3267576
Patent Document 2: JP 3310662
Patent Document 3: WO 02/31192
Patent Document 4: JPA 2002-355081
Patent Document 5: WO 03/029441
Patent Document 6: WO 92/20702
Non-Patent Document 1: Marshall, A., Hodgson, J. DNA chips: an array of possibilities. Nat. Biotechnol. 16, 27-31, 1998.
Non-Patent Document 2: Koshkin A A et al. Tetrahedron 1998. 54, 3607-3630.
Non-Patent Document 3: Koshkin A A et al. J. Am. Chem. Soc. 1998. 120, 13252-13253.
Non-Patent Document 4: Wahlestedt C et al. PNAS. 2000. 97, 5633-5638.
Non-Patent Document 5: H. C. Birnboim. J. Doly, Nucleic Acids Res., 7, 1513 (1979)

DISCLOSURE OF THE INVENTION

Problems to be Solved by the Invention

However, according to research conducted by the present inventors, it has been clarified that in the case of the PALSAR method using a uniform reaction temperature, a self-assembly substance is formed uniformly in the reaction solution, so that in the gene detection by a signal amplifying technique using a uniform reaction temperature, an HCP self-assembly substance formation reaction in the reaction solution not on target gene is prioritized over an HCP self-assembly substance formation reaction on target genes bonding to the solid-phase.

FIG. 5 shows a schematic explanatory drawing of an example of a signal amplifying technique by the PALSAR method using a uniform reaction temperature, (a) shows the self-assembly substance formation at a uniform reaction temperature, (b) shows the self-assembly substance bonded to a target gene after being washed after the self-assembly substance formation reaction. As shown in FIG. 5, it has been clarified that a sufficient signal amplifying effect is obtained only by the self-assembly substance being formed on the target gene; however, the self-assembly substance being formed in the reaction solution not on the target gene is removed by the subsequent washing procedure, so that the amount of the signal amplification is decreased in comparison with the total amount of the self-assembly substance formed by the reaction.

The object of the present invention is to provide a hybridization method for realizing an effective hybridization reaction, a target gene detecting method with high sensitivity using the hybridization method, and a signal amplifying method for improving the detection sensitivity of a target gene to a great degree.

Means for Solving the Problem

For solving the above-mentioned problems, the present inventors have earnestly researched on how to improve the formation efficiency of the HCP self-assembly substance on the target gene, and as a result thereof, found that by forming partially a reaction temperature region in the reaction solution, the formation efficiency of the HCP self-assembly substance on the target gene can be improved markedly, and further, not only in the HCP self-assembly reaction, but also in the other normal hybridization reaction, by forming partially a reaction temperature region in the reaction solution, the efficiency of hybrid formation on the target gene can be improved markedly. According to the findings, the present inventors have reached the present invention.

That is, the hybridization method of the present invention comprises the use of oligonucleotides in a reaction solution, the method comprising, forming partially a reaction temperature region in the reaction solution, and performing a hybridization reaction in the reaction temperature region.

In the present invention, there is not imposed any special limitation on the hybridization reaction, but it is preferable that the hybridization reaction includes a self-assembly reaction forming a double-stranded self-assembly substance by hybridizing plural kinds of oligonucleotide probes having complementary base sequence regions hybridizable to each other to self-assemble the oligonucleotides.

As a first example, the plural kinds of oligonucleotide probes comprise a pair of oligonucleotide probes consisting of a first probe and a second probe, the first probe having at least three nucleic acid regions, a nucleic acid region X, a nucleic acid region Y and a nucleic acid region Z in order from 5'-end and having the structure of the following chemical formula (1), and the second probe having at lease three nucleic acid regions, a nucleic acid region X', a nucleic acid region Y' and a nucleic acid region Z' in order from 5'-end and having the structure of the following chemical formula (2) (Patent Documents 1 and 2).

[Chemical formula 1]

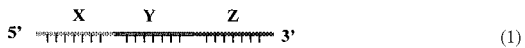

(1)

[Chemical formula 2]

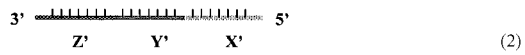

(2)

(In the above chemical formulae (1) and (2), each of X-X', Y-Y' and Z-Z' is complementary nucleic acid regions hybridizable to each other.)

FIG. 1 to FIG. 3 are schematic explanatory drawings showing examples of a self-assembly reaction using a pair of oligonucleotide probes (a pair of HCPs) consisting of a first probe (a first HCP) and a second probe (a second HCP) each comprising 3 nucleic acid regions. As shown in FIG. 1 to FIG. 3, using a plurality of a pair of oligonucleotide probes 18 having the structures of the chemical formulae (1) and (2) (FIG. 1), the pairs are hybridized such that they cross in alternation (FIG. 2) to form a double-stranded self-assembly substance (polymer) 20 (FIG. 3).

As a second example, the plural kinds of oligonucleotide probes comprise: a dimer forming probe series having n groups of plural pairs of dimer forming probes consisting of a first group to a (2n–1)-th (n≧1) group in order, in which each of a pair of No. 1 and No. 2 oligonucleotides is divided to 3 regions of a 3'-end region, a middle region and a 5'-end region, a base sequence of the middle region of each oligonucleotide is complementary to each other, and a base sequence of the 3'-end region and a base sequence of the 5'-end region of each oligonucleotide are not complementary to each other; and a cross-linking probe series having n groups of plural pairs of cross-linking probes consisting of a second group to a 2n-th group in order, in which each of a pair of No. 1 and No. 2 oligonucleotides is divided to 2 regions of a 3'-end region and a 5'-end region, and a base sequence of the 3'-end region and a base sequence of the 5'-end region of each oligonucleotide are not complementary to each other; and wherein the base sequence of the cross-linking probe is cross-linkable with plural pairs of dimers formed from the dimer forming probes (Patent Document 4).

There is exemplified a self-assembly reaction forming a self-assembly substance by hybridizing the oligonucleotide probes to self-assemble the oligonucleotides. It is preferable that in the hybridization of the probes, after the dimer forming probes are hybridized to form the dimers (dimer probes) of each group, the dimers are hybridized with the cross-linking probes to form the self-assembly substance.

In the second example using the plural kinds of oligonucleotide probes, in the case of n=1, there are two combinations of the complementary base sequences between the first series of dimer forming probes and the second series of cross-linking probes.

There is an example in the case of n=1 as follows. The probes may be usable in which each of the following pairs of the base sequences is complementary to each other:
the 3'-end region of No. 1 oligonucleotide of the first group and the 3'-end region of No. 1 oligonucleotide of the second group,
the 5'-end region of No. 2 oligonucleotide of the first group and the 5'-end region of No. 2 oligonucleotide of the second group,
the 3'-end region of No. 2 oligonucleotide of the second group and the 3'-end region of No. 2 oligonucleotide of the first group, and
the 5'-end region of No. 1 oligonucleotide of the second group and the 5'-end region of No. 1 oligonucleotide of the first group.

There is another example in the case of n=1 as follows. The probes may be usable in which each of the following pairs of the base sequences is complementary to each other:
the 3'-end region of No. 1 oligonucleotide of the first group and the 3'-end region of No. 1 oligonucleotide of the second group,
the 5'-end region of No. 2 oligonucleotide of the first group and the 5'-end region of No. 1 oligonucleotide of the second group,
the 3'-end region of No. 2 oligonucleotide of the first group and the 3'-end region of No. 2 oligonucleotide of the second group, and
the 5'-end region of No. 1 oligonucleotide of the first group and the 5'-end region of No. 2 oligonucleotide of the second group.

In the second example of plural kinds of oligonucleotide probes, in the case of n≧2, there are two combinations of complementary base sequences between the dimer forming probe series containing the first, the third, . . . , and the (2n–1)-th groups, and the cross-linking probe series containing the second, the fourth, . . . , and the (2n)-th groups. There is an example in the case of n≧2 as follows. The probes may be usable in which each of the following pairs of the base sequences is complementary to each other:
the 3'-end region of No. 1 oligonucleotide of the (2n–3)-th group and the 3'-end region of No. 1-oligonucleotide of the (2n–2)-th group, the 5'-end region of No. 2 oligonucleotide of the (2n–3)-th group and the 5'-end region of No. 2-oligonucleotide of the (2n–2)-th group, the 3'-end region of No. 2 oligonucleotide of the (2n–2)-th group and the 3'-end region of No. 2-oligonucleotide of the (2n–1)-th group, the 5'-end region of No. 1 oligonucleotide of the (2n–2)-th group and the 5'-end region of No. 1-oligonucleotide of the (2n–1)-th group, the 3'-end region of No. 1 oligonucleotide of the last group of the dimer forming probe series and 3'-end region of No. 1 oligonucleotide of the last group of the cross-linking probe series, the 5'-end region of No. 2 oligonucleotide of the last group of the dimer forming probe series and the 5'-end region of No. 2 oligonucleotide of the last group of the cross-linking probe series, the 3'-end region of No. 2 oligonucleotide of the last group of the cross-linking probe series and the 3'-end region of No. 2 oligonucleotide of the first group of the dimer forming probe series, and the 5'-end region of No. 1 oligonucleotide of the last group of the cross-linking probe series and the 5'-end region of No. 1 oligonucleotide of the first group of the dimer forming probe series.

There is another example in the case of $n \geqq 2$ as follows. The probes may be usable in which each of the following pairs of the base sequences is complementary to each other:

the 3'-end region of No. 1-oligonucleotide of the (2n–3)-th group and the 3'-end region of No. 1 oligonucleotide of the (2n–2)-th group, the 5'-end region of No. 2 oligonucleotide of the (2n–3)-th group and the 5'-end region of No. 2 oligonucleotide of the (2n–2)-th group, the 3'-end region of No. 2 oligonucleotide of the (2n–2)-th group and the 3'-end region of No. 2 oligonucleotide of the (2n–1)-th group, the 5'-end region of No. 1 oligonucleotide of the (2n–2)-th group and the 5'-end region of No. 1 oligonucleotide of the (2n–1)-th group, the 3'-end region of No. 1 oligonucleotide of the last group of the dimer forming probe series and the 3'-end region of No. 1 oligonucleotide of the last group of the cross-linking probe series, the 5'-end region of No. 2 oligonucleotide of the last group of the dimer forming probe series and the 5'-end region of No. 1 oligonucleotide of the last group of the cross-linking probe series, the 3'-end region of No. 2 oligonucleotide of the last group of the cross-linking probe series and the 3'-end region of No. 2 oligonucleotide of the first group of the dimer forming probe series, and the 5'-end region of No. 2-oligonucleotide of the last group of the cross-linking probe series and the 5'-end region of No. 1 oligonucleotide of the first group of the dimer forming probe series.

The self-assembly reaction using the second example of the plural kinds of oligonucleotide probe will be concretely described. For example, in the case of n=1, a dimmer probe having a structure of the chemical formula (3) formed with a pair of dimer forming probes is hybridized with a pair of cross-linking probes having a structure of the chemical formula (4), or a pair of cross-linking probes having a structure of the chemical formula (5) to form a self-assembly substance having a structure of the chemical formula (6).

[Chemical formula 3]

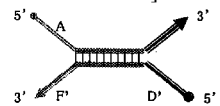

(3)

[Chemical formula 4]

(4)

[Chemical formula 5]

(5)

(In the above chemical formulae (3) to (5), each of A-A', B-B', C-C', D-D' and F-F' is complementary nucleic acid regions hybridizable to each other.)

[Chemical formula 6]

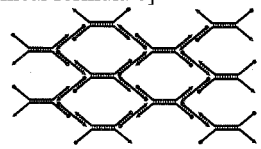

(6)

As a third example, the plural kinds of oligonucleotide probes comprise: plural pairs of dimer forming probes having plural groups of dimer forming probes consisting of a first group to a k-th ($n \geqq 2$) group in order, in which each of a pair of No. 1 and No. 2 oligonucleotides is divided to 3 regions of a 3'-end region, a middle region and a 5'-end region, a base sequence of the middle region of each oligonucleotide is complementary to each other, and a base sequence of the 3'-end region and a base sequence of the 5'-end region of each oligonucleotide are not complementary to each other; and each of the following pairs of the base sequences of the probes is complementary to each other (Patent Document 3):

(a) the 3'-end region of No. 1 oligonucleotide of the (k–1)-th group and the 3'-end region of No. 2 oligonucleotide of the k-th group, (b) the 5'-end region of No. 2 oligonucleotide of the (k–1)-th group and the 5'-end region of No. 1 oligonucleotide of the k-th group, (c) the 3'-end region of No. 1 oligonucleotide of the last group and the 3'-end region of No. 2 oligonucleotide of the first group, (d) the 5'-end region of No. 2 oligonucleotide of the last group and the 5'-end region of No. 1 oligonucleotide of the first group.

As a fourth example, the plural kinds of oligonucleotide probes comprise: plural pairs of dimer forming probes having plural groups of dimer forming probes consisting of a first group to a k-th ($n \geqq 2$) group in order, in which each of a pair of No. 1 and No. 2 oligonucleotides is divided to 3 regions of a 3'-end region, a middle region and a 5'-end region, a base sequence of the middle region of each oligonucleotide is complementary to each other, and a base sequence of the 3'-end region and a base sequence of the 5'-end region of each oligonucleotide are not complementary to each other; and wherein each of the following pairs of the base sequences of the probes is complementary to each other: and each of the following pairs of the base sequences of the probes is complementary to each other (Patent Document 3):

(a) the 3'-end region of No. 1-oligonucleotide of the (k–1)-th group and the 3'-end region of No. 2-oligonucleotide of the k-th group, (b) the 5'-end region of No. 1-oligonucleotide of the (k−1)-th group and the 5'-end region of No. 2-oligonucleotide of the k-th group,
(c) the 3'-end region of No. 1-oligonucleotide of the last group and the 3'-end region of No. 2-oligonucleotide of the first group,
(d) the 5'-end region of No. 1-oligonucleotide of the last group and the 5'-end region of No. 2-oligonucleotide of the first group.

In the third and fourth examples of the plural kinds of oligonucleotide probes, there is exemplified a self-assembly reaction forming a self-assembly substance by hybridizing plural pairs of dimer forming probes of the first group to the k-th group to self-assemble the oligonucleotides. It is preferable that in the hybridization of the probes, after the dimer forming probes are hybridized in each group to form the dimers (dimer probes) therein, the dimer probes of each group are hybridized to form the self-assembly substance.

The self-assembly reaction using the third or fourth examples of the plural kinds of oligonucleotide probe will be concretely described. For example, in the case of k=2, a dimer probe having a structure of the chemical formula (7) formed with a pair of dimer forming probes is hybridized with a dimer probe having a structure of chemical formula (8) formed with a pair of dimer forming probes, or a dimer probe having a structure of the chemical formula (9) formed with a pair of dimer forming probes to form a self-assembly substance having a structure of the chemical formula (10).

[Chemical formula 7]

(7)

[Chemical formula 8]

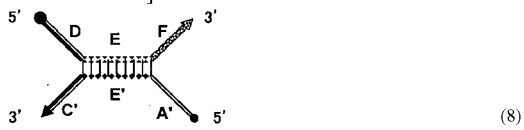

(8)

[Chemical formula 9]

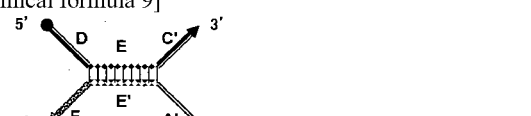

(9)

(In the above chemical formulae (3) to (5), each of A-A', B-B', C-C', D-D' and F-F' is complementary nucleic acid regions hybridizable to each other.)

[Chemical formula 10]

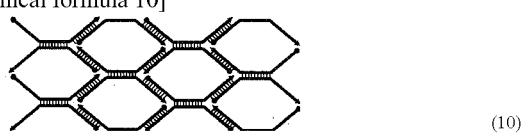

(10)

The signal amplifying method of the present invention resides in the method, wherein the detection sensitivity of a target gene in a reaction device for detecting a gene is improved using a self-assembly reaction forming a double-stranded self-assembly substance by hybridizing plural kinds of oligonucleotide probes having complementary base sequence regions hybridizable to each other to self-assemble the oligonucleotides, and wherein the self-assembly reaction is performed using the hybridization method of the present invention.

There is preferably used an assist probe having a region complementary to each base sequence of the target gene and the oligonucleotide probe to bind the target gene to the oligonucleotide probe. Further, at least one of the oligonucleotide probes to be used for the self-assembly reaction may include a complementary base sequence at a part of the target gene.

According to the signal amplifying method of the present invention, a target gene can be detected with high sensitivity by detecting the formed self-assembly substance. There are imposed no special limitations on the method for detecting the self-assembly substance. It is preferable that, for example, at least one of the oligonucleotide probes to be used for the self-assembly reaction is labeled with a labeling substance in advance, and the self-assembly substance is detected by detecting the labeling substance. There are imposed no special limitations on the labeling substances and the known labeling substances are widely usable. As the labeling substance, for example, a radioisotope, a fluorescent substance, a luminous substance, a coloring substance, a coloring enzyme or a luminous enzyme can be used.

Also, with a self-assembly substance formed by the self-assembly reaction of the oligonucleotides bound to the target genes, it is possible to detect the self-assembly substance by hybridizing the self-assembly substance with a labeled probe. As the labeled probe, a substance labeled with a coloring enzyme, a luminous enzyme or a radioisotope and the like can be used.

Further, with a fluorescent substance bindable to a nucleic acid being added to the self-assembly substance, the presence of the self-assembly substance is detectable by a photochemical change of the fluorescent substance. It is preferable for the fluorescent substance to have the capability of being insertable into a double-stranded base pair.

A first aspect of a method for detecting a target gene of the present invention comprises the use of the signal amplifying method of the present invention.

A second aspect of a method for detecting a target gene of the present invention comprises the use of a hybridization reaction of oligonucleotides in a reaction solution to detect a gene, wherein the hybridization reaction includes a hybridization reaction carried out using the hybridization method of the present invention. It is preferable that at least one oligonucleotide to be used for the hybridization reaction has a complementary base sequence to a part of the target gene.

In the present invention, there are imposed no special limitations on the reaction devices for detecting a gene, and there can be used various kinds of reaction devices for detecting a gene. As the reaction devices, especially, a microplate, a DNA microarray, a magnetic particle and the like are suitable for use.

In the present invention, a single-stranded DNA and/or RNA and a double-stranded DNA and/or RNA can be used as the target gene. Also a gene containing SNPs (Single Nucleotide Polymorphisms) can be used as the target gene.

In the present invention, it is preferable that the oligonucleotide used for the hybridization reaction is labeled in advance by a labeling substance and the labeling substance is detected to detect the target gene. The labeling substance has no special limitations and the known labeling substances can be widely used. For example, there can be used a radioisotope, a fluorescent substance, a luminous substance, a coloring substance, a coloring enzyme, a luminous enzyme or the like as the labeling substance.

The oligonucleotide usually consists of DNA or RNA, and a nucleic acid analog also can be used. As a nucleic acid analog, for example, peptide nucleic acid (PNA, Patent Document 6) or Locked Nucleic Acid (LNA, Non-Patent Documents 2 to 4) is applicable. Further, a pair of oligonucleotide probes usually consists of the same kind of nucleic acid; however, for example, a pair of a DNA probe and an RNA probe may be also applicable. That is, the kind of the nucleic acid to be used for the probe can be selected from DNA, RNA or a nucleic acid analog (e.g. PNA, LNA or the like). Further, in the present invention the nucleic acid composition in one probe is not limited to only one kind, for example, DNA alone, and there can be used, for example, an oligonucleotide probe (a chimera probe) consisting of DNA and RNA as occasion demands.

The length of each complementary base sequence region of the oligonucleotide probe is at least 5 bases, preferably from 10 to 100 bases, and more preferably from 15 to 30 bases.

These probes can be synthesized by known methods. For example, a DNA probe can be synthesized by a phosphoamitide method using the DNA synthesizer 394-type made by Applied Biosystems Japan Ltd. Also, there are known as other methods an organophosphoric acid triester method, an H-phosphonate method, a thiophosphonate method and others. There can be used the probes synthesized by any kinds of methods.

The number of the oligonucleotide probes to be used in the present invention is not limited and can be adjusted in the range of from $10^2$ to $10^{15}$. There are imposed particularly no limitations on the compositions or the concentrations of the reaction buffer solution and a usual buffer solution to be commonly used for the nucleic acid amplification can be used. The suitable pH value may be in the commonly usable range, and preferably from 7.0 to 9.0. The reaction temperature applicable to the partial reaction temperature region is from 40 to 80° C., and preferably from 55 to 65° C.

As a specimen for measuring a target gene (DNA or RNA) in the present invention, any specimen that would potentially contain the corresponding nucleic acids may be used. The target genes may be either prepared or isolated appropriately from the specimen, and is not particularly limited. For example, there are given as the specimens ones derived from an organism such as blood, serum, urine, feces, cerebrospinal fluid, tissue fluid, cell cultures or the like, ones which may contain or be infected with viruses, bacteria, fungi or the like, and so on. Further, nucleic acids such as DNA or RNA in which a target gene in a specimen has been amplified by a known method.

Results of the Invention

According to the present invention, the detection sensitivity of the target gene is markedly improved with ease. Also according to the present invention, the hybrid forming efficiency in a hybridization reaction is improved. Further, according to the present invention, formation of the self-assembly substance to be used for detection is increased and the signal amplification is improved.

DESCRIPTION OF REFERENCE NUMERALS

10: a microplate, 12: a target gene, 14: a capture probe, 15: a labeling substance, 16: an assist probe, 17: one of a pair of HCPs, 18: a pair of HCPs, 20: a self-assembly substance, 22: a hot plate, 24: a cooling means, 50: an assist probe-1, 51: an assist probe-2, 52: a target gene, 53: a probe A, 54: a capture probe-1, 55: an assist probe-3, 56: a capture probe-2, 57: a probe B, 58: a capture probe 3, 59: a probe C, 60: a target gene.

BEST MODE FOR CARRYING OUT THE INVENTION

Several embodiments of the present invention will hereinafter be described with reference to the accompanying drawings. It goes without saying, however, that these embodiments are merely illustrative, and a variety of modifications may be made without departing from the spirit and scope of the present invention.

There are three ways of heat transmission; heat conduction (collision of molecules), heat convection (movement of matter) and heat emission (an electromagnetic wave). In a hybridization method of the present invention, utilizing the ways of the heat transmission, a temperature of a reaction solution in a platform such as a microplate is not uniform and a reaction temperature region is partially formed in the reaction solution.

Figure 1:
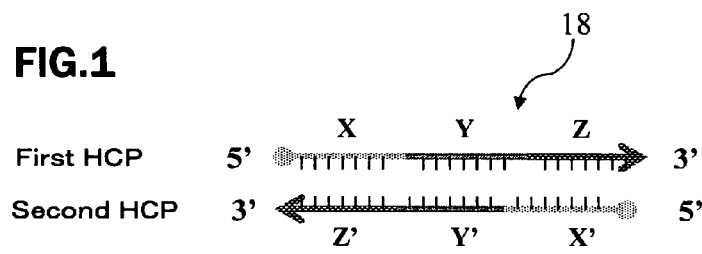
FIG. 1 is a schematic explanatory view of a pair of HCPs.
Figure 2:
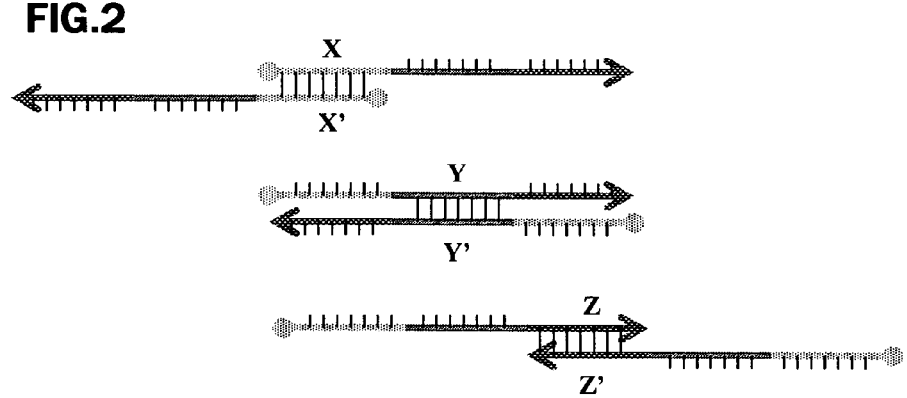
FIG. 2 is a schematic explanatory view of a binding aspect of a pair of HCPs.
Figure 3:
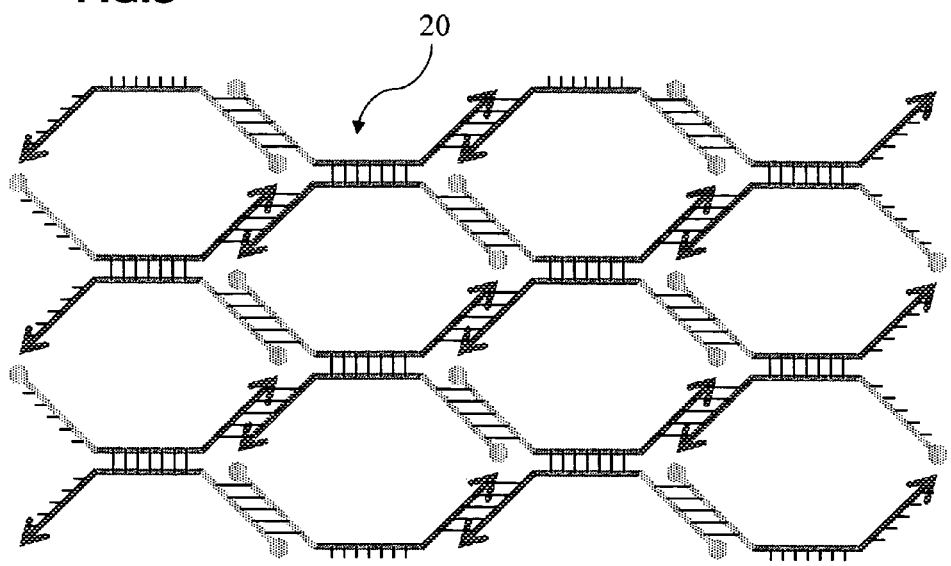
FIG. 3 is a schematic explanatory view of a self-assembly substance formed with plural pairs of HCPs.
Figure 4:
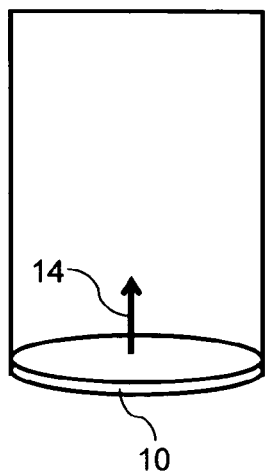
FIG. 4 is a schematic explanatory view of an embodiment of a signal amplifying method in a microplate using the PALSAR method.
Figure 4:
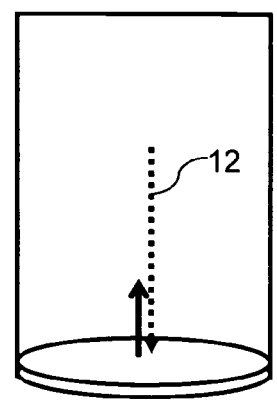
Figure 4:
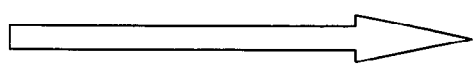
Figure 4:
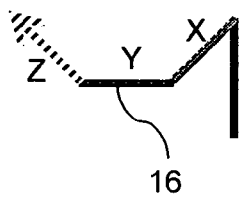
Figure 4:
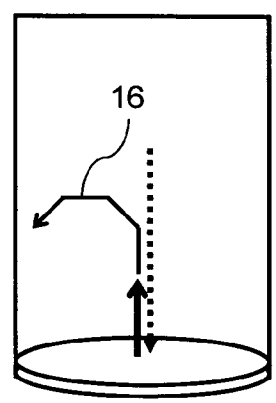
Figure 4:
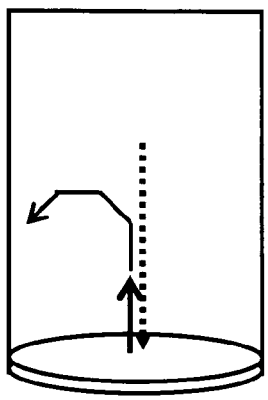
Figure 4:
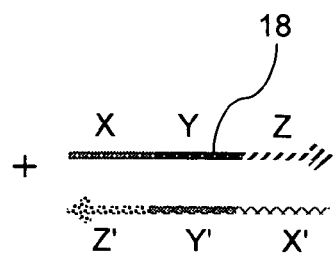
Figure 4:
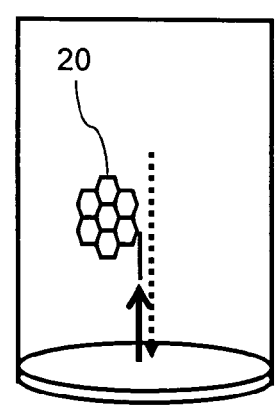
Figure 5:
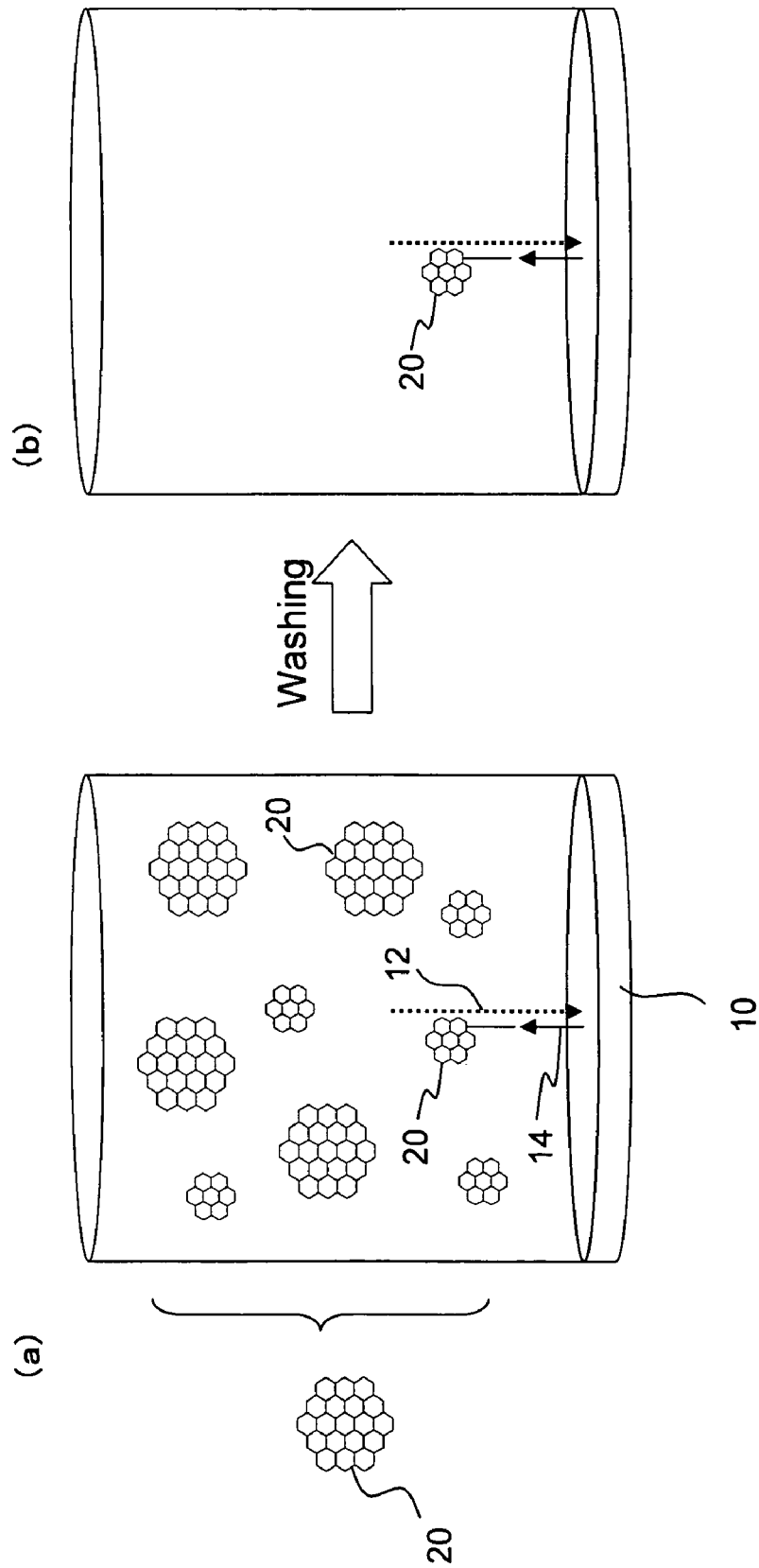
FIG. 5 is a schematic explanatory view of an embodiment of a signal amplifying method with the PALSAR method using a uniform reaction temperature.
Figure 8:
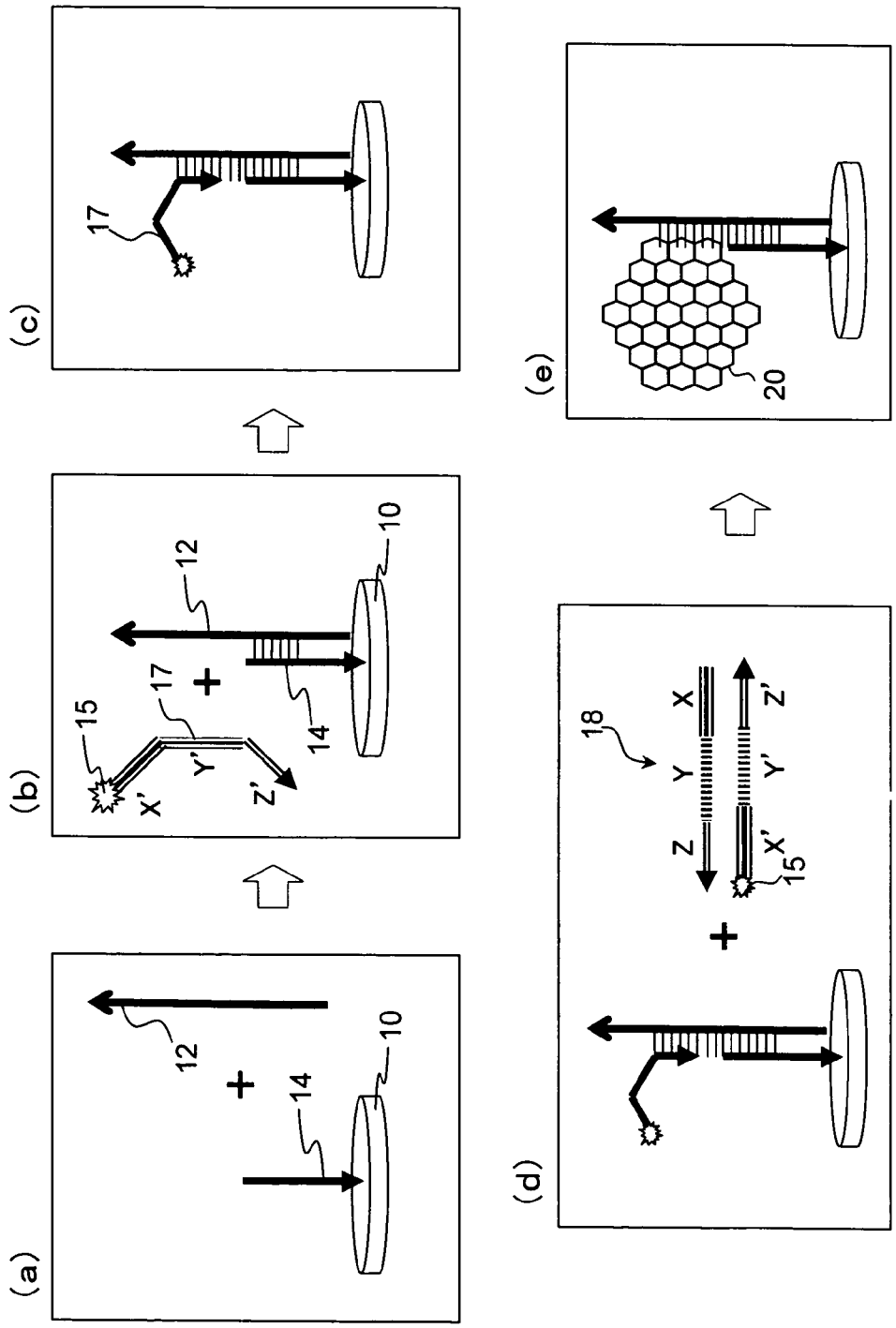
FIG. 8 is a schematic explanatory view of another embodiment of a method for detecting a target gene with a signal amplifying technique using a partial reaction temperature region according to the present invention.

The formation of the partial reaction temperature region is applicable to a gene detection technique using a hybridization reaction, and preferably to a gene detection technique with a signal amplifying technique especially using the PALSAR method shown in FIG. 4 and FIG. 8. In the present invention, the reaction temperature region is partially formed in the vicinity of a portion on which the target gene is fixed such as the bottom portion of a detection platform, and a hybridization reaction is preferentially carried out at the bottom portion of the detection platform, by which it is possible to perform the gene detection with high sensitivity.

Next, an embodiment for forming a partial reaction temperature region in a hybridization reaction will be concretely described.

In the present invention, by keeping only a part of a reaction solution to a temperature suitable for hybridization, a hybridization reaction is effectively carried out at the part only so that the detection of a target gene using the hybridization can be carried out with high sensitivity. The present invention may include any hybridization reaction wherein only a part of the reaction solution is kept to a reaction temperature. It is preferable to form a high temperature region and a low temperature region in the reaction solution to make a temperature gradient for keeping only a part of the reaction solution to the reaction temperature. Further it is more preferable to form the high temperature region by heating and the low temperature region by cooling. Also it is preferable to cool off the reaction solution in advance such that the hybridization reaction is not carried out.

Figure 6:
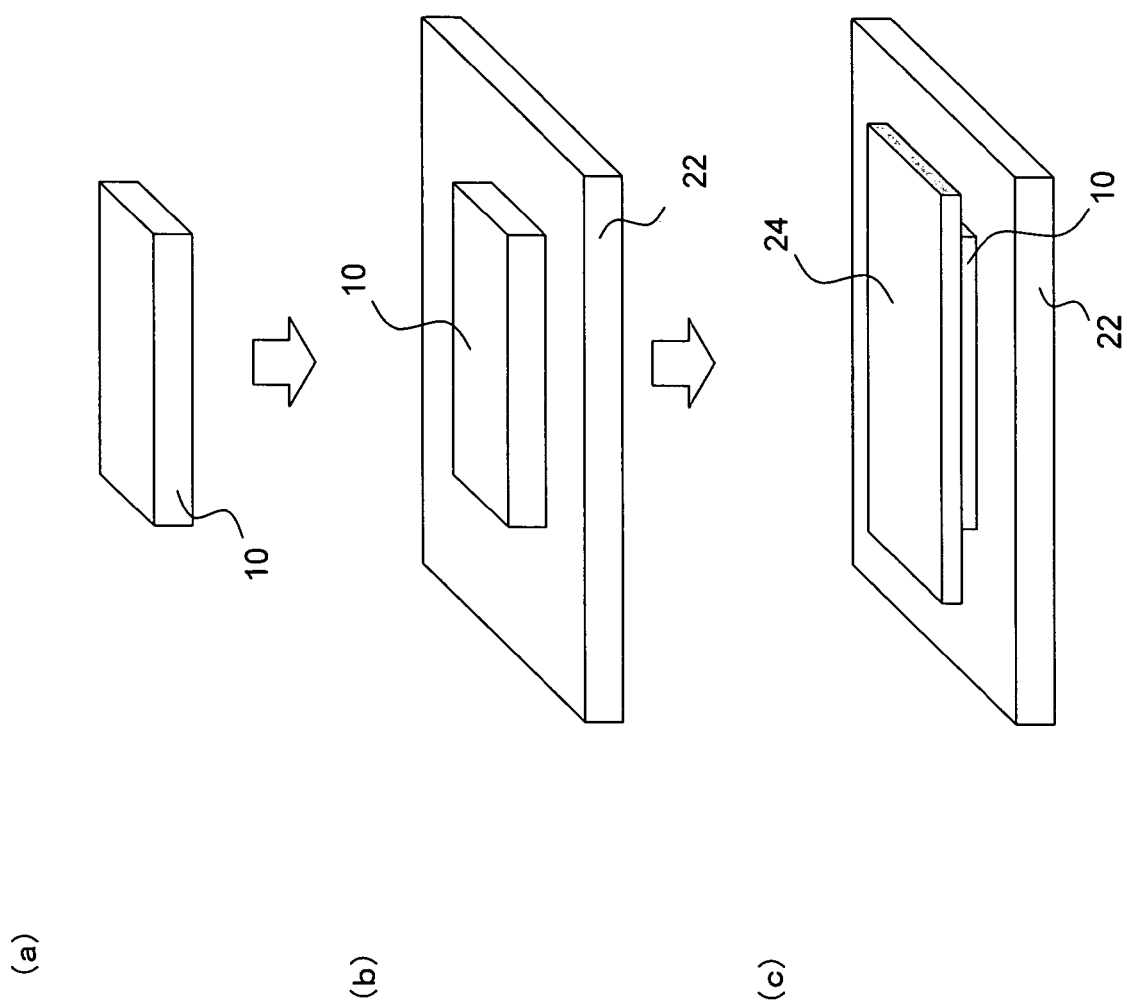
FIG. 6 is a schematic explanatory view of an embodiment of a method for detecting a target gene with a microplate using a partial reaction temperature region.

There is concretely exemplified the hybridization method using a partial reaction temperature region with a microplate shown in the schematic explanatory drawing of FIG. 6. The method for detecting a target gene of the present invention will be hereinafter described with reference to the case where a microplate is used as a reaction platform. Incidentally, any platform other than the microplate may be also applicable in the same way as the microplate.

At first, after oligonucleotides to be used for the hybridization reaction are added to a microplate 10 having captured a target gene, the microplate 10 is entirely cooled off to 4° C. [FIG. 6(*a*)]. After the cooling off, as shown in FIG. 6(*b*), the microplate 10 is put on a heating means such as a hot plate 22 which has been adjusted in advance to a suitable temperature for the hybridization reaction, and further a cooling means 24 such as a cold insulator (−20° C.) or similar cooling plates, for example, a cooled aluminum block is put on the microplate 10 to carry out the hybridization reaction [FIG. 6(*c*)].

The hybridization reaction is preferably carried out such that the reaction solution is heated and cooled using an apparatus equipped with the heating means and the cooling means, and the heating means and the cooling means are preferably controllable in temperature. When the hybridization reaction is carried out with a microplate, the heating means and the cooling means each preferably has a structure with a flat surface contacting the microplate, and especially the bottom surface of the microplate is preferably capable of being both heated and cooled.

Figure 7:
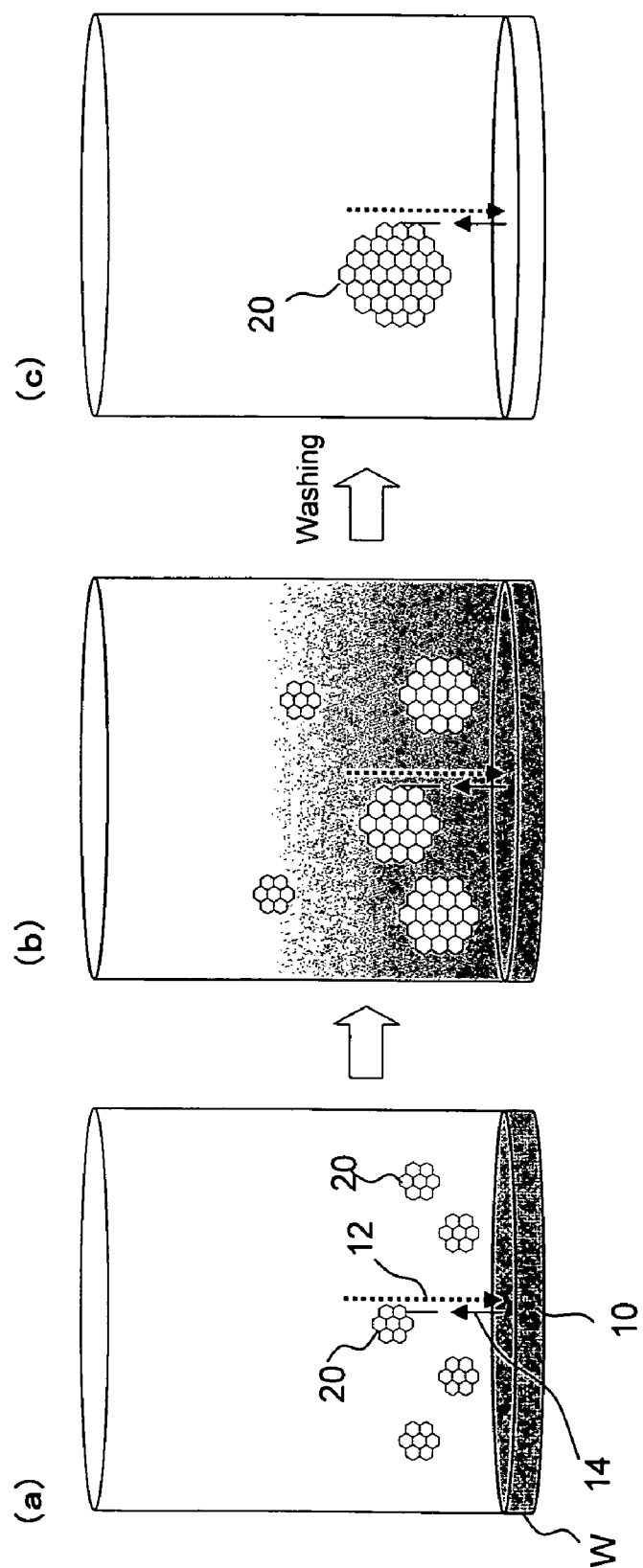
FIG. 7 is a schematic explanatory view of an embodiment of a method for detecting a target gene with a signal amplifying technique using a partial reaction temperature region according to the present invention.

Further an embodiment for performing a self-assembly reaction as the hybridization reaction will be concretely described. FIG. 7 is an schematic explanatory view of an embodiment of a gene detection method by a signal amplifying technique wherein a partial reaction temperature region is formed in a microplate, and the embodiment shows the case where the self-assembly reaction of steps (e) to (f) in FIG. 4 is carried out using the hybridization method of the present invention.

As showed in FIG. 4(*e*) mentioned above, after adding the plural kinds of oligonucleotide probes to be used for the self-assembly reaction to the microplate 10 having captured the target gene, the microplate 10 is cooled off. After the cooling off, as shown in FIG. 7(*a*), by setting a most suitable temperature for the self-assembly reaction to a layer portion W (the bottom portion of the microplate 10) in the vicinity of the target gene 12, the hybridization reaction is carried out only at the layer portion. As shown in FIG. 7(*b*), with the lapse of the reaction time, the temperature of the microplate 10 reaches the temperature suitable for the self-assembly reaction from the bottom portion to the upper portion of the microplate 10, so that after washing the microplate 10, as shown in FIG. 7(*c*), a large self-assembly substance is bound only to the target gene 12 to detect the gene with high sensitivity.

FIG. 8 is an schematic explanatory view of another embodiment of a gene detection method by a signal amplifying technique wherein a partial reaction temperature region is formed in a microplate. FIG. 8 shows an embodiment of a signal amplifying technique using a pair of HCPs wherein a region of one of a pair of HCPs is complementary to the target gene. According to the PALSAR method, as shown in FIG. 8(*a*), a capture probe 14 for capturing a gene is bound to the bottom portion of a detection platform (a microplate 10, a DNA microarray or the like), a target gene 12 (e.g. *E. coli*-16SrRNA and the like) is captured through the steps of FIG. 8(*b*) to FIG. 8(*d*), an HCP 17 having a region complementary to the target gene is added to the target gene 12 [FIG. 8(*b*)], the target gene 12 is bound to the HCP 17 [FIG. 8(*c*)], as shown in FIG. 8(*d*), plural pairs of HCPs 18 are added and a self-assembly substance 20 is formed by a self-assembly reaction to perform the signal amplification.

According to the present invention, in the self-assembly reaction of the steps of FIG. 8(*d*) to FIG. 8(*e*), a partial reaction temperature region is formed at the bottom portion of the detection platform where the target gene is present, and the self-assembly reaction is carried out preferentially at the bottom portion of the detection platform, so that the formation efficiency of the self-assembly substance is markedly improved on the target gene [FIG. 8(*e*)] and as a result the gene detection is possible with high sensitivity. Incidentally, FIG. 8 shows the embodiment where one of a pair of HCPs to be used for the self-assembly reaction is labeled with a labeling substance in advance and the self-assembly substance is detected by detecting the labeling substance; however, a method for detecting the self-assembly substance is not particularly limited.

EXAMPLES

In the following, the present invention will be described more concretely in conjunction with several examples. It goes without saying, however, that the examples are only illustrative and should not be interpreted as being restrictive.

Experimental Examples 1 and 2

Formation of a Self-assembly Substance by the PALSAR Method Using a Pair of Probes in Accordance with the Differences of the Reaction Temperature and the Reaction Time <Method of Preparation of Each Solution>

(1) Preparation of a Hybridization Solution

Following reagents are prepared and used as hybridization solutions.

Hybridization Solution-1

[4×SSC, 0.2% SDS, 1% Blocking reagent (made by La Roche Ltd.)]

(2) Preparation of a Hybridization-HCP Solution.

A pair of probes (HCP-1 and HCP-2) described below is dissolved to the hybridization solution-1 to the concentration of 2 pmol/μL and used as the hybridization-HCP solution.

```
Base sequence of HCP-1 (SEQ ID NO:1)
5'-X region (CATGTCTCGTGTCTTGCATC)

Y region (CTGCTACAGTGAACACCATC)

Z region (GTTCTCGACATAGACCAGTC)-3'

Base sequence of HCP-2 (SEQ ID NO:2)
(5'-end labeled with digoxigenin)
DIG-5'-X' region (GATGCAAGACACGAGACATG)

Y' region (GATGGTGTTCACTGTAGCAG)

Z' region (GACTGGTCTATGTCGAGAAC)-3'
```

<Reaction and Detection Method>

The hybridization-HCP solution was divided by 20 µL each and poured into 128 microtubes of each 0.2 mL capacity, and after the half of the microtubes each was heated at 94° C. for 30 seconds (Experimental Example 1) or another half thereof each was cooled off on the ice (Experimental Example 2), the microtubes are subjected to respective reaction temperatures of 37.0, 39.6, 41.4, 43.8, 46.4, 48.7, 50.5, 53.0, 55.0, 57.1, 58.7, 60.6, 62.8, 64.6, 66.0 or 68.0° C.) for 30 minutes, 1 hour or 3 hours respectively and are rapidly cooled off on the ice. The results of these experiments are confirmed with the 0.5% agarose gel electrophoresis method.

Figure 9:
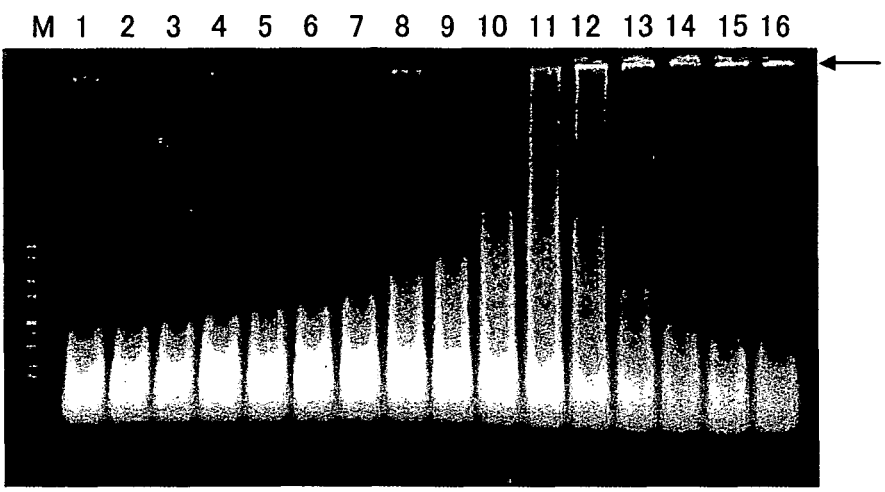
FIG. 9 is pictures showing the results of Example 1.
Figure 9:
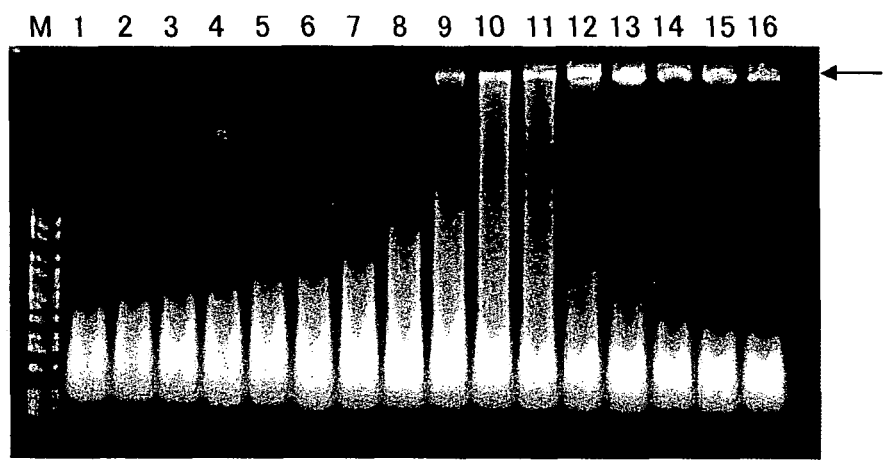
Figure 9:
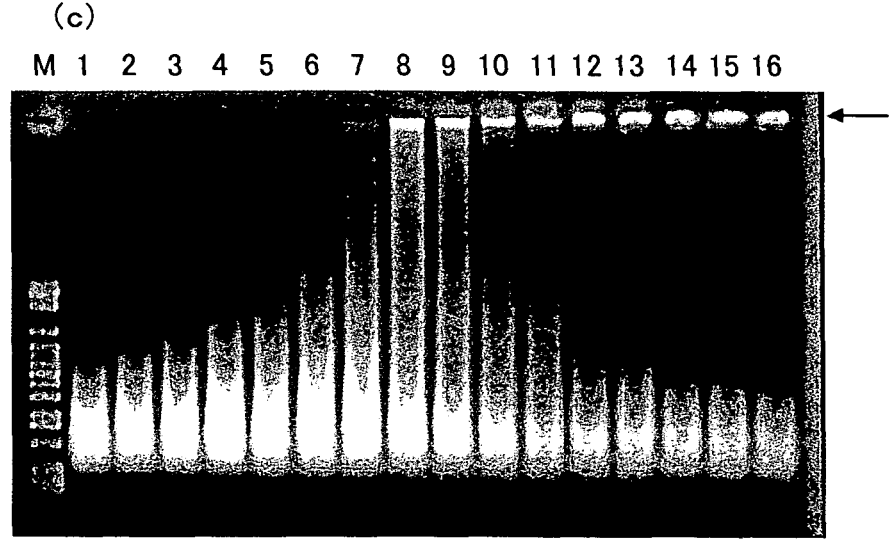
Figure 10:
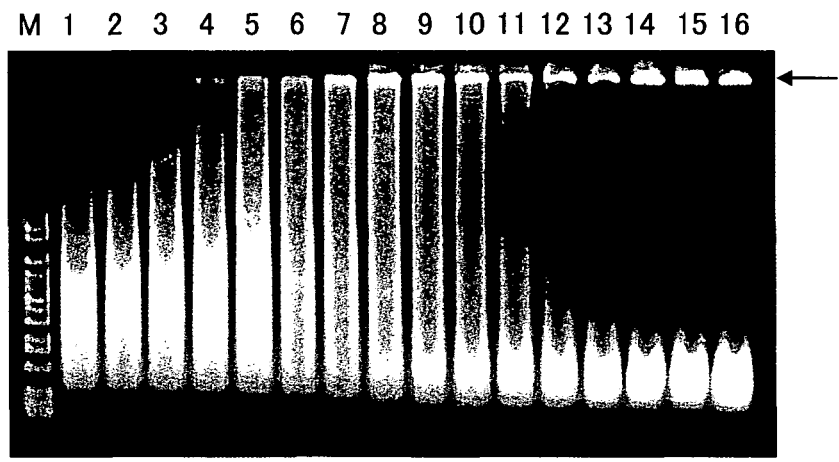
FIG. 10 is pictures showing the results of Example 2.
Figure 10:
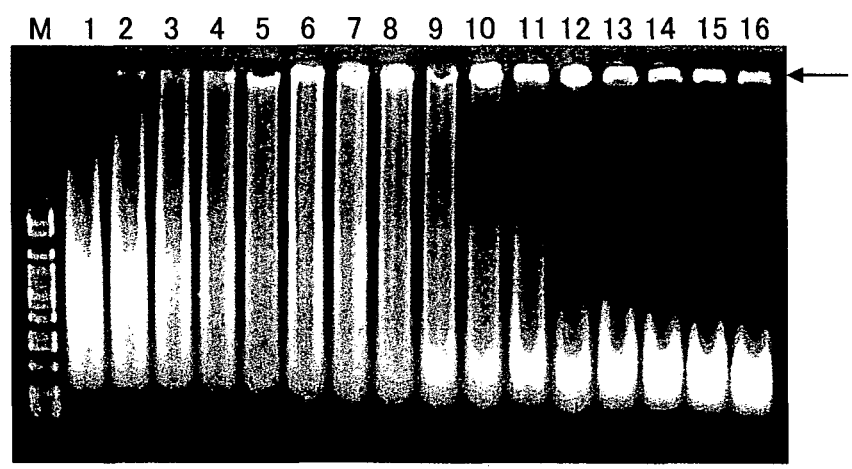
Figure 10:
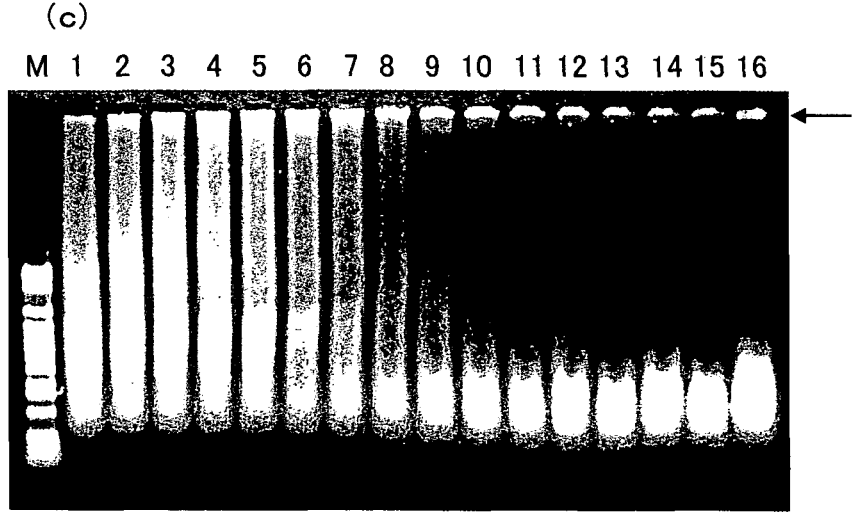

FIG. 9 is a photograph showing the results of Experimental Example 1 and FIG. 10 is a photograph showing the results of Experimental Example 2. In FIG. 9 and FIG. 10, the part (a) shows the results of the cases of 30 minutes reaction in each reaction temperature, the part (b): 1 hour reaction in each reaction temperature and the part (c): 3 hours reaction in each reaction temperature. Further, in FIG. 9 and FIG. 10, the temperature conditions of each sample lane are as follows.

M: size marker, 1: 37.0° C., 2: 39.6° C., 3: 41.4° C., 4: 43.8° C., 5: 46.4° C., 6: 48.7° C., 7: 50.5° C., 8: 53.0° C., 9: 55.0° C., 10: 57.1° C., 11: 58.7° C., 12: 60.6° C., 13: 62.8° C., 14: 64.6° C., 15: 66.0° C., 16: 68.0° C.

As shown in FIG. 9, in Experimental Example 1 where the heat denaturation was performed at 94° C., in any reaction time, it was recognized that the self-assembly substance, the size of which is enough to pile up in an agarose gel well, was formed at 55° C. or higher (the arrows in the figure). On the other hand, as shown in FIG. 10, in Experimental Example 2 where the heat denaturation was not performed, it was recognized that the self-assembly substance was formed at 55° C. or higher as in Experimental Example 1; however, smear bands which are considered as non-specific cohesion of HCPs were recognized at below 55° C., and the same tendency is recognized even after the reaction time was extended. Hence, under the conditions of the hybridization-HCP solution used in these Experimental Examples, the reaction temperature suitable for formation of the self-assembly substance consisting of a pair of probes (HCP-1 and 2) was at around 55° C.

Examples 1 to 3 and Comparative Examples 1 to 3

Measurement of Detection Sensitivity of a Target Gene by a Hybridization Reaction Using a Partial Reaction Temperature Region Examples 1 to 3 each shows the results of the cases each where a partial reaction temperature region was formed in the reaction solution of the hybridization reaction using the HCPs in comparison with the results of the control cases each where a reaction solution with a uniform reaction temperature was used (Comparative Examples 1 to 3). Hereinafter, the condition wherein the reaction is carried out with the formed partial reaction temperature region referred to as "C/H", the condition wherein the reaction is carried out with the uniform reaction temperature is referred to as "H/H".

In the case of a reaction using the HCPs, a self-assembly reaction using a pair of HCPs (HCP-1 and HCP-2) is referred to as "2HCP", a hybridization reaction using only a single-stranded HCP (HCP-1 or HCP-2) is referred to as "1HCP".

<Preparation of Each Solution>

(1) Preparation of a Hybridization Solution

The following reagents are prepared to make hybridization solutions, which were used in Examples 1 to 3 and Comparative Examples 1 to 3.

Hybridization Solution-1:
[4×SSC, 0.2% SDS, 1% Blocking reagent (made by La Roche Ltd.)]
Hybridization Solution-2:
[4×SSC, 0.2% SDS, 1% Blocking reagent (made by La Roche Ltd.), 20% formamide, Salmon sperm DNA (10 µg/mL)]
Hybridization Solution-3:
[4×SSC, 0.2% SDS, 1% Blocking reagent (made by La Roche Ltd.), 5% PEG 20000]

(2) Preparation of the Lysis Solution

*Staphylococcus aureus* cultured for 18 hours in the triptic soy agar was suspended in a physiological saline solution to prepare an undiluted solution of cultured micro-organisms. The solution was diluted by the physiological saline solution to a given number of micro-organisms. The diluted solution was subjected to bacteriolysis in accordance with the alkali-SDS method (Non-Patent Document 5) to make the lysis solution containing target rRNA which is used in Examples 1 to 3 and Comparative Examples 1 to 3. The given number of micro-organisms was calculated from the number of viable micro-organisms obtained such that a dilution series of the diluted solutions of cultured micro-organisms was made and the diluted solutions were cultured with the triptic soy agar.

Example 1 and Comparative Example 1

Figure 11:
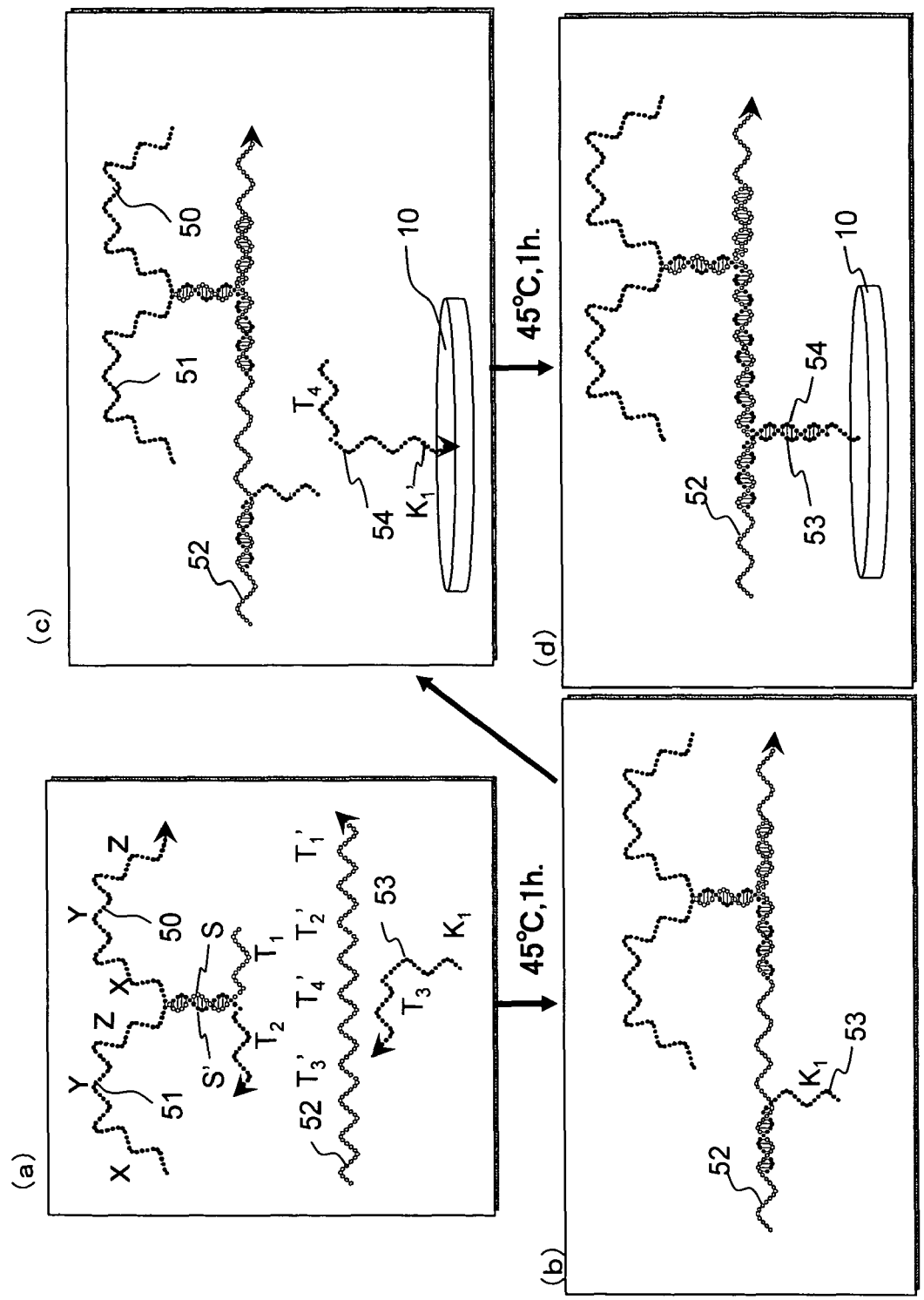
FIG. 11 is a schematic explanatory view showing a flow-chart of Example 1.

There were compared the results of the detection sensitivity of the target gene and the formation efficiency of the self-assembly substance on the target gene between "C/H" and "H/H" conditions. The schematic explanatory view of Example 1 is shown in FIG. 11.

<Preparation of Each Solution>

(1) Preparation of the First Hybridization Probe Solution

10 µL of the following assist probe-1 (100 pmol/µL), 10 µL of the following assist probe-2 (100 pmol/µL), 10 µL of the following probe A (100 pmol/µL) and 70 µL of the hybridization solution-2 were poured into a 0.2 mL microtube, mixed by a mixer, heated for 30 seconds at 94° C., and immediately cooled on the ice to prepare a probe mixed solution.

The probe mixed solution was poured into a 15 mL conical tube into which the hybridization solution-2 was divided by 3.9 mL and poured, mixed by a mixer to prepare the first hybridization probe solution (the final concentration of each probe was 0.25 pmol/µL) to be used for hybridizing the target rRNA and the capture probe.

```
Base sequence of the assist probe-1
(Reference numeral 50 in FIG. 11) (SEQ ID NO: 3)
```

```
-continued
5'-T₁ region (TAGCTAATGCAGCGCGGATCC)

S   region (GAGAAAGTTCATAGATATAC)

X   region (CATGTCTCGTGTCTTGCATC)

Y   region (CTGCTACAGTGAACACCATC)

Z   region (GTTCTCGACATAGACCAGTC)-3'

Base sequence of the assist probe-2
(Reference numeral 51 in FIG. 11) (SEQ ID NO: 4)
5'-X region (CATGTCTCGTGTCTTGCATC)

Y   region (CTGCTACAGTGAACACCATC)

Z   region (GTTCTCGACATAGACCAGTC)

S'  region (GTATATCTATGAACTTTCTC)

T₂ region (ATCTATAAGTGACAGCAAGAC)-3'

Base sequence of the probe A
(Reference numeral 53 in FIG. 11) (SEQ ID NO: 5)
5'-K₁ region (CGACGACGACGACGACGACG)

T₃ region (GCGGTTCAAAATATTATCCGG)-3'
```

(2) Preparation of the Second Hybridization-HCP Solution

30 μL each of HCP-1 (100 pmol/μL) and HCP-2 (100 pmol/μL) described in Experimental Example 1 and 40 μL of the hybridization solution-1 were poured into a 0.2 mL microtube, mixed by a mixer, heated for 30 seconds at 94° C. and immediately cooled on the ice to prepare an HCP mixed solution.

This HCP mixed solution was poured into a 15 mL conical tube into which the hybridization solution-1 was divided by 1.9 mL and poured, mixed by a mixer to prepare the second hybridization HCP solution (the final concentration of each probe was 1.5 pmol/μL), which was used in Example 1-1 and Comparative Example 1-1.

Also, a second hybridization-HCP solution to be used in Example 1-2 and Comparative Example 1-2 was prepared in the same procedure described above except that 30 μL of sterilized water was used instead of the HCP-1.

<Preparation of a Microplate>

The following capture probe-1 having a sequence complementary to rRNA of *Staphylococcus aureus* was fixed on the strip well type 96 well microplate and used in Example 1, Example 3, Comparative Example 1 and Comparative Example 3.

```
Base sequence of the capture probe-1
(Reference numeral 54 in FIG. 11) (SEQ ID NO: 6)
5'-T₄ region (CGTCTTTCACTTTTGAACCAT)

K₁' region (CGTCGTCGTCGTCGTCGTCG)-3'-Amino link
```

<Reaction and Detection Method>

(1) The First Hybridization

800 μL of the lysis solution (the concentration of microorganisms: 1×10⁵ CFU/mL) prepared as above and 800 μL of the first hybridization probe solution was poured into a 2.0 mL microtube, mixed by a mixer and heated at 45° C. for 1 hour. The parts (a) and (b) of FIG. 11 are schematic explanatory views of the above reaction steps. Also as a control, the same reaction steps were carried out except that a physiological saline solution was used instead of the lysis solution.

This reaction solution was divided by 100 μL each and poured into the strip well type 96 well microplate prepared as above, sealed fixedly by a plate sealer, and further reacted at 45° C. for 1 hour. The parts (c) and (d) of FIG. 11 are schematic explanatory views of the above reaction steps. After the above reaction, the 96 well microplate was washed by a washing solution (50 mM-Tris, 0.3M-NaCl, 0.01%-Triton X-100, pH 7.6).

(2) The Second Hybridization (a Reaction for Forming a Self-assembly Substance or a Hybrid Using the HCP)

After the washing, the second hybridization HCP solution was divided by 50 μL each and poured into the 96 well microplate from which the washing solution removed sufficiently, and sealed fixedly by a plate sealer.

In Example 1, that is Example 1-1 and Example 1-2, half of the strip wells of the microplates were used and the reactions were carried out at the "C/H" condition. The "C/H" condition in Example 1 was as follows. After the strip wells were cooled at 4° C. in a refrigerator for 30 minutes, the cooled strip wells were set on an aluminum block for microplate use (weight: 828 g, width: 12.1 cm, diameter: 8.2 cm and height: 4.2 cm) of an ammonium block thermostatic bath (CoolStat, manufactured by Anatech), a cooling device (a lid of StrataCooler, manufactured by STRATAGENE) is put on the microplate, the reaction temperature of the thermostatic bath was set at 45° C. or 55° C., and the reaction was carried out for 1 hour.

In Comparative Example 1, that is Comparative Example 1-1 and Comparative Example 1-2, the other half of the above strip wells were used and the reaction was carried out at the "H/H" condition. The "H/H" condition in Comparative Example 1 was as follows.

The strip wells were stood at a room temperature for 30 minutes, and the reaction was carried out for 1 hour using an incubator set at 45° C. or 55° C.

(3) Detection

After the microplate wells were washed, 50 μL of POD labeled anti-digoxigenin (60 mU/mL) dissolved in 50 mM-Tris (pH 7.6) was poured thereinto, and the reaction was carried out using an incubator set at 37° C. After washing the microplate wells with a washing solution, 50 μL of a coloring solution containing a 0.2 M acetic acid buffer solution (pH 5.0), 0.06% TMB and 0.04% $H_2O_2$ was added and stood for 15 minutes in a dark place, and the absorbance thereof at 655 nm was measured. The results of the measurements are shown in Table 1 and 2.

TABLE 1

| | Absorbance at 45° C. of the reaction temperature in the second hybridization | | | |
|---|---|---|---|---|
| Number of micro-organisms | Example 1 (C/H) | | Comparative Example 1 (H/H) | |
| (CFU/mL) | 1-1(2HCP) | 1-2(1HCP) | 1-1(2HCP) | 1-2(LHCP) |
| 0 | 0.035 | 0.036 | 0.036 | 0.034 |
| 1 × 10⁵ | 0.646 | 0.343 | 0.186 | 0.266 |

TABLE 2

Absorbance at 55° C. of the reaction temperature
in the second hybridization

| Number of micro-organisms (CFU/mL) | Example 1 (C/H) | | Comparative Example 1 (H/H) | |
|---|---|---|---|---|
| | 1-1(2HCP) | 1-2(1HCP) | 1-1(2HCP) | 1-2(1HCP) |
| 0 | 0.038 | 0.035 | 0.035 | 0.035 |
| $1 \times 10^5$ | 0.490 | 0.241 | 0.114 | 0.122 |

As shown in Tables 1 and 2, in the both cases of 1HCP and 2HCP, the measured value of Example 1 under the C/H condition is higher than that of Comparative Example 1 under the H/H condition; therefore, by using the C/H condition the hybridization reaction was effectively carried out on the target gene.

Also in Example 1 under the C/H condition, the measured values in Example 1-1 having used 2HCP were higher than those in Example 1-2 having used 1HCP; on the other hand, in Comparative Example 1 under the H/H condition, the measured values in Comparative Example 1-2 having used 2HCP were the same as or less than those in Comparative Example 1-2 using 1HCP. From these results, it was confirmed that the self-assembly substance was formed more effectively on the target gene under the C/H condition wherein the reaction temperature in the solution was formed stepwise than under the H/H condition wherein the reaction temperature was uniform.

Example 2 and Comparative Example 2

Figure 12:
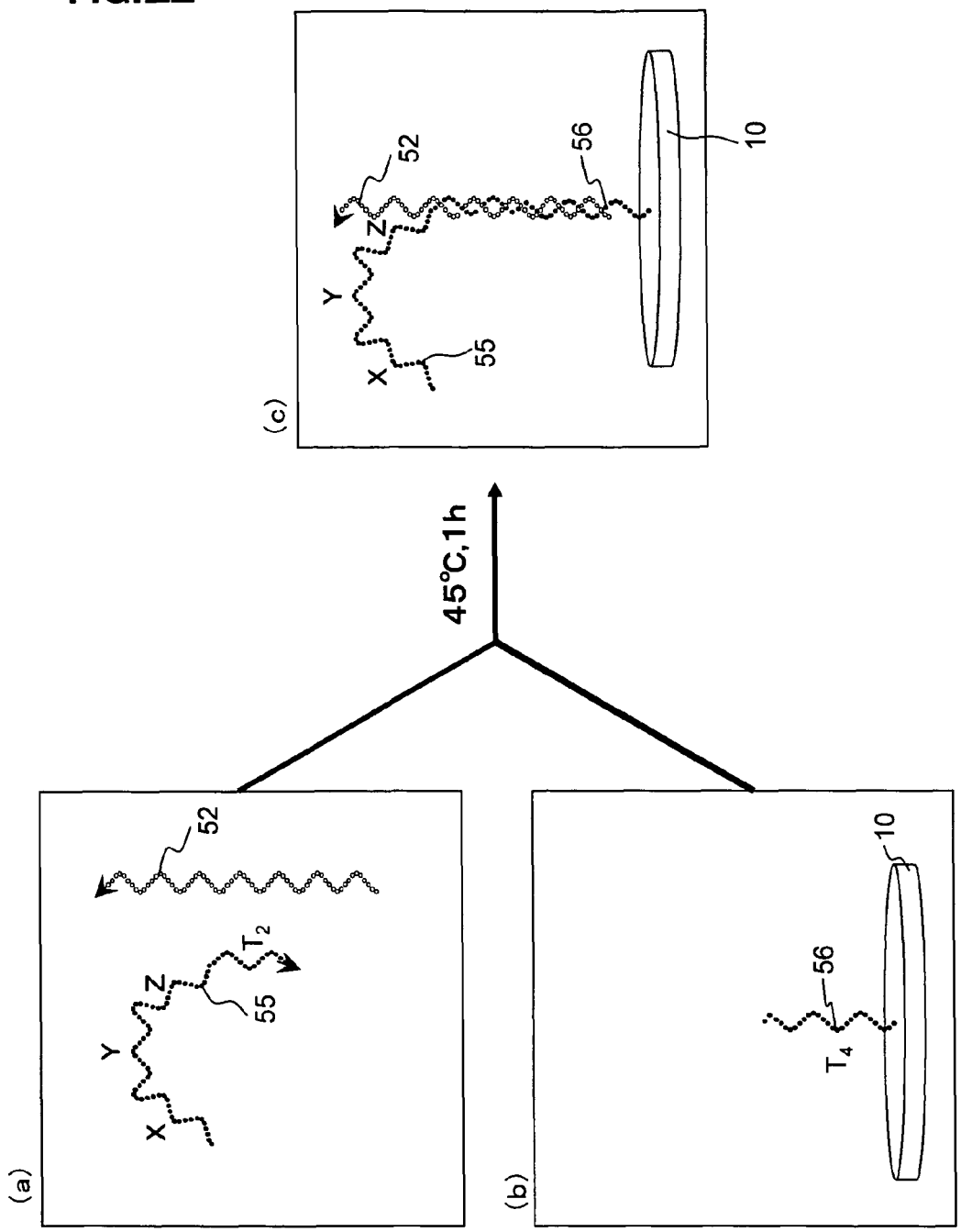
FIG. 12 is a schematic explanatory view showing a flow-chart of Example 2.

Formation of the stepped reaction temperature in the C/H condition is confirmed by changing the volume of the reaction solution in the formation of the hybrid or the self-assembly substance with the HCPs. The schematic explanatory view of Example 2 is shown in FIG. 12.

<Method of Preparation of Each Solution>

(1) Preparation of the First Hybridization Probe Solution

20 μL of the following assist probe-3 (100 pmol/μL) and 80 μL of the hybridization solution-2 were poured into a 0.2 mL microtube, mixed by a mixer, heated at 94° C. for 30 seconds, and immediately cooled on the ice to prepare the first hybridization probe solution.

```
Base sequence of the assist probe-3
(Reference numeral 55 in FIG. 12) (SEQ ID No: 7)
5'-X  region (CATGTCTCGTGTCTTGCATC)

Y  region (CTGCTACAGTGAACACCATC)

Z  region (GTTCTCGACATAGACCAGTC)

T₂ region (ATCTATAAGTGACAGCAAGAC)-3'
```

The probe solution was poured into a 15 mL conical tube into which the hybridization solution-2 was divided by 7.9 mL each and poured, and mixed by a mixer to prepare the first hybridization probe solution (the final conc. of the probe: 0.25 pmol/μL) to be used for hybridization with the target rRNA and the capture probe.

(2) Preparation of the Second Hybridization-HCP Solution

32 μL of each the HCP-1 (100 pmol/μL) and the HCP-2 (100 pmol/μL) described in Example 1, 36 μL of the hybridization solution-1 were poured into a 0.2 mL microtube, mixed by a mixer and heated at 94° C. for 30 seconds, then immediately followed by being cooled on the ice to prepare three HCP mixed solutions.

The HCP mixed solution was poured into each of three 15 mL conical tubes into which the hybridization solution-1 was divided by 1.5 mL each and poured, and mixed by a mixer to prepare the second hybridization HCP solution (each final conc.: 2 pmol/μL).

Also, a second hybridization-HCP solution to be used in Example 2-2 and Comparative Example 2-2 was prepared in the same procedure described above except that 32 μL of sterilized water was used instead of the HCP-1.

<Preparation of a Microplate>

The following capture probe-2 having a sequence complementary to rRNA of *Staphylococcus aureus* was fixed on the strip well type 96 well microplate and used in Example 2 and Comparative Example 2.

```
Base sequence of the capture probe-2
(Reference numeral 56 in FIG. 12) (SEQ ID NO: 8)
5'-T₄ region (CGTCTTTCACTTTTGAACCAT)-3'-Amino link
```

<Reaction and Detection Method>

(1) The First Hybridization

50 μL of the lysis solution (the concentration of microorganisms: $1 \times 10^5$ CFU/mL) prepared as above and 50 μL of the first hybridization probe solution were poured dividedly into the strip well type 96 well microplate prepared as above, sealed fixedly by a plate sealer, and further reacted at 45° C. for 1 hour. FIG. 12 is a schematic explanatory view of the above reaction steps. Also as a control, the same reaction steps were carried out except that a physiological saline solution was used instead of the lysis solution.

After the above reaction, the microplate was washed by a washing solution using a plate washer.

(2) The Second Hybridization (A Reaction for Forming a Self-assembly Substance or a Hybrid Using the HCP)

After the washing, the second hybridization HCP solution was divided by 50 μL or 100 μL each and poured into the 96 well microplate from which the washing solution removed sufficiently, and sealed fixedly by a plate sealer.

In Example 2, that is Example 2-1 and Example 2-2, half of the strip wells of the microplates were used and the reactions were carried out at 50° C. or 55° C. for 1 hour under the "C/H" condition. Incidentally, the "C/H" condition was the same as in Example 1 except that a cold insulator was used as a cooling means and the temperature setting of the thermostatic bath was changed.

In Comparative Example 2, that is Comparative Example 2-1 and Comparative Example 2-2, the other half of the above strip wells were used and the reaction was carried out at 50° C. or 55° C. for 1 hour under the "H/H" condition. The "H/H" condition is the same as in Comparative Example 1 except that a microplate heater (manufactured by Digene Corporation.) was used instead of the incubator and the temperature setting was changed.

(3) Detection

The absorbance was measured by the same procedure as in Example 1. The results are shown in Tables 3 and 4. Incidentally, each of the absorbance values shown in Tables 3 and 4 was obtained by subtracting the measured value of the control experiment where the physiological saline solution was used instead of the lysis solution from the above measured value.

TABLE 3

Absorbance at 50° C. of the reaction temperature in the second hybridization

| Reaction solution (μL) | Number of micro-organisms (CFU/mL) | Example 2 (C/H) 2-1 (2HCP) | Example 2 (C/H) 2-2 (1HCP) | Comparative Example 2 (H/H) 2-1 (2HCP) | Comparative Example 2 (H/H) 2-2 (1HCP) |
|---|---|---|---|---|---|
| 50 | $1 \times 10^5$ | 0.233 | 0.053 | 0.034 | 0.052 |
| 100 | $1 \times 10^5$ | 0.290 | 0.177 | 0.211 | −0.007 |

TABLE 4

Absorbance at 55° C. of the reaction temperature in the second hybridization

| Reaction solution (μL) | Number of micro-organisms (CFU/mL) | Example 2 (C/H) 2-1 (2HCP) | Example 2 (C/H) 2-2 (1HCP) | Comparative Example 2 (H/H) 2-1 (2HCP) | Comparative Example 2 (H/H) 2-2 (1HCP) |
|---|---|---|---|---|---|
| 50 | $1 \times 10^5$ | 0.230 | 0.144 | 0.053 | 0.006 |
| 100 | $1 \times 10^5$ | 0.228 | 0.142 | 0.083 | −0.006 |

As shown in Tables 3 and 4, in Example 2 under the C/H condition, the measured values of Example 2-1 having used 2HCP were higher than that of Example 2-2 using 1HCP, and were higher in comparison with those of Comparative Example 2-1 having used 2HCP under the H/H condition. Also regarding 1HCP, in Example 2-2 under the C/H condition, the measured value was increased when the volume of the reaction solution was increased from 50 μL to 100 μL; however, in Comparative Example 2-2 under the H/H condition the change of the measured value was not observed by changing the volume of the reaction solution. From these results, it was confirmed that the reaction temperature in the solution was formed in a more stepped state under the C/H condition, so that the self-assembly substance was more easily formed on the target gene and at the same time the hybridization efficiency of the usual single-stranded probes not using the PALSAR method was improved.

Example 3 and Comparative Example 3

Figure 13:
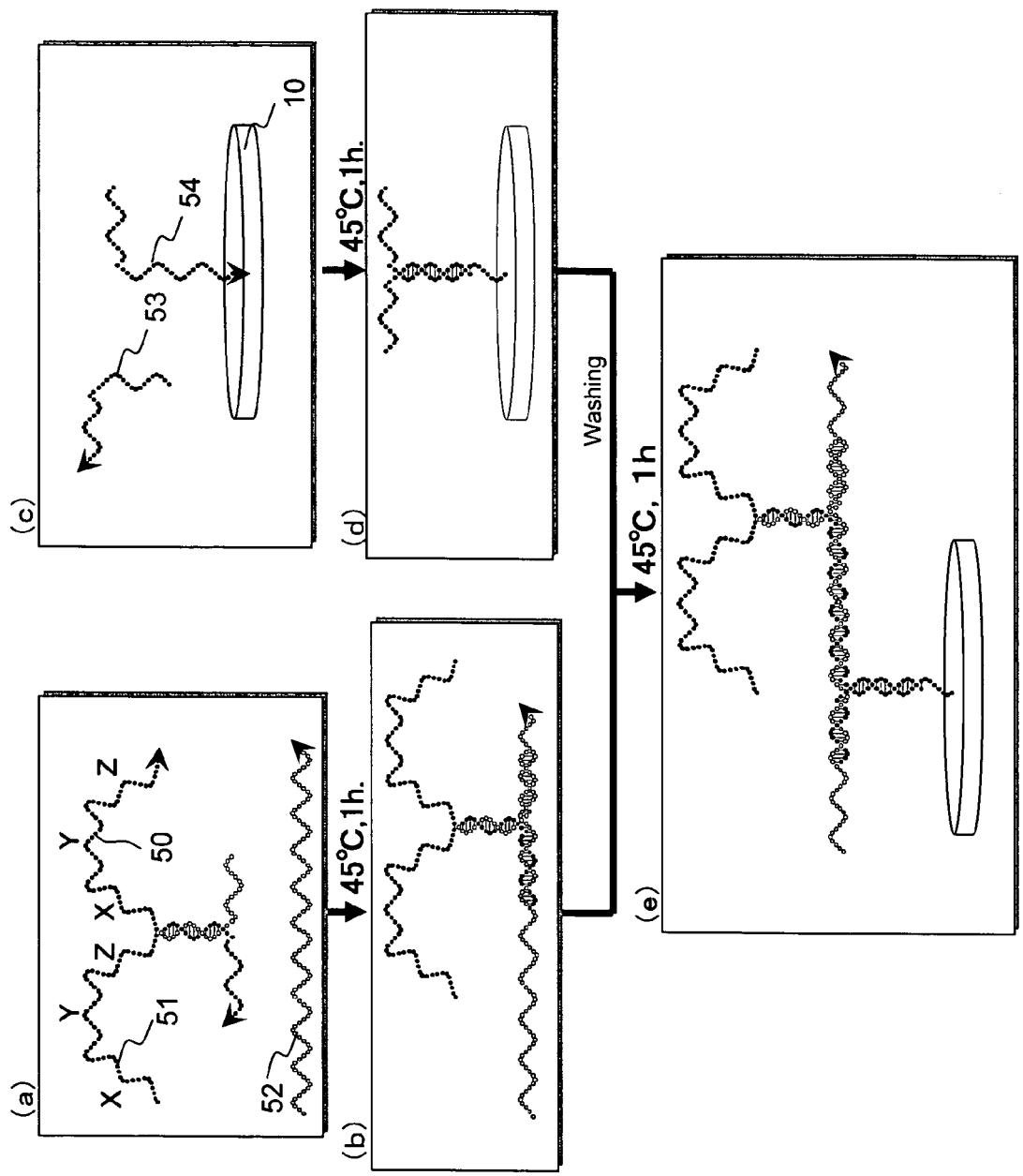
FIG. 13 is a schematic explanatory view showing a flow-chart of Example 3.

By varying the reaction solution volume for the second hybridization using the partial reaction temperature region, it was confirmed the effects on the hybridization efficiency of the single-stranded probes and the formation efficiency of the self-assembly substance by the HCPs. A schematic explanatory view of Example 3 is shown in FIG. 13.

<Preparation of Each Solution>

(1) Preparation of the First Hybridization Probe Solution-1
10 μL of the assist probe-1 solution (100 pmol/μL), the assist probe-2 solution (100 pmol/μL) described in Example 1 and 80 μL of the hybridization solution-2 were added to a 0.2 mL microtube, mixed by a mixer, heated at 80° C. for 30 seconds, and immediately cooled on the ice to prepare the probe mixed solution.

The probe solution was poured into a 15 mL conical tube into which the pre-cooled hybridization solution-2 was divided by 3.9 mL each and poured, and mixed by a mixer to prepare the first hybridization probe solution-1 (the final conc. of the probes: 0.25 pmol/μL) to be used for hybridization with the target rRNA.

(2) Preparation of the First Hybridization Probe Solution-2
10 μL of the probe A solution (100 pmol/μL) described in Example 1 and 90 μL of the hybridization solution-2 were poured into a 0.2 mL microtube, mixed by a mixer, heated at 80° C. for 30 seconds, and immediately cooled on the ice to prepare the probe mixed solution.

The probe mixed solution is poured into a 15 mL conical tube into which the pre-cooled hybridization solution-2 was divided by 1.9 mL each and poured, and mixed by a mixer to prepare the first hybridization probe solution-2 (the final conc. of the probes: 0.25 pmol/μL) to be used for hybridization with the target rRNA and the capture probe.

(3) Preparation of the Second Hybridization-HCP Solution
40 μL of each the HCP-1 (100 pmol/μL) and the HCP-2 (100 pmol/μL) described in Experimental Example 1, 20 μL of the hybridization solution-1 were poured into a 0.2 mL microtube, mixed by a mixer, heated at 80° C. for 30 seconds, and then immediately cooled on the ice to prepare the HCP mixed solution.

The HCP mixed solution was poured into a 15 mL conical tube into which the hybridization solution-1 was divided by 1.9 mL each and poured, and mixed by a mixer to prepare the second hybridization HCP solution (each final conc.: 2 pmol/μL) which was used in Example 3-1 and Comparative Example 3-1.

Also, a second hybridization-HCP solution to be used in Example 3-2 and Comparative Example 3-2 was prepared in the same procedure described above except that 40 μL of sterilized water was used instead of the HCP-1.

<Reaction and Detection Method>

(1) The First Hybridization
50 μL of the first hybridization probe-2 solution was poured into the strip well type 96 well microplate described in Example 1, sealed fixedly by a plate sealer, and further reacted at 45° C. for 1 hour. The parts (c) and (d) of FIG. 13 are schematic explanatory views of the above reaction steps.

After the above reaction, the microplate was washed by a washing solution using a plate washer.

At the same time, 500 μL of the lysis solution of $5 \times 10^4$ CFU/mL prepared by the above-mentioned method or a physiological saline solution (as a control), and 500 μL of the first hybridization probe solution-1 were poured into a 1.5 mL microtube, mixed by a mixer, and reacted at 45° C. for 1 hour. The parts (a) and (b) of FIG. 13 are schematic explanatory views of this reaction steps.

This reaction solution was divided by 100 μL each and poured into the microplate which was subjected to the reaction with the first hybridization probe solution, sealed fixedly by a plate sealer, and further reacted at 45° C. for 1 hour. The parts (b), (d) and (e) of FIG. 13 are schematic explanatory views of the above reaction steps.

After the above reaction, the microplate was washed by a washing solution with a plate washer.

(2) The Second Hybridization (a Reaction for Forming a Self-assembly Substance or a Hybrid Using the HCP)
After the washing, the second hybridization HCP solution was divided by 50 μL or 100 μL each and poured into the 96 well microplate from which the washing solution removed sufficiently, and sealed fixedly by a plate sealer.

In Example 3, that is Example 3-1 and Example 3-2, half of the strip wells of the microplates were used and the reactions were carried out under the "C/H" condition. The "C/H" condition in Example 3 was as follows.

After the strip wells were cooled at 4° C. in a refrigerator for 30 minutes, the cooled strip wells were set on a microplate heater (manufactured by DIGENE), an aluminum block pre-cooled at 4° C. in a refrigerator was put on the microplate, a cooling device (a lid of StrataCooler manufactured by STRATAGENE) was put on the microplate, the reaction temperature of the thermostatic bath was set at 55° C., and the reaction was carried out for 1 hour.

In Comparative Example 3, that is Comparative Example 3-1 and Comparative Example 3-2, the other half of the above strip wells were used and the reaction was carried out at 55° C. for 1 hour under the "H/H" condition. The "H/H" condition in Comparative Example 3 was the same as Comparative Example 2 except that the temperature setting was changed.

In Example 3 and Comparative Example 3, mineral oil was dropped onto each block before the reaction so as to improve close adherence to the strip well.

(3) Detection

The absorbance was measured by the same procedure as in Example 1. The results are shown in Table 5. Incidentally, each of the absorbance values shown in Table 5 was obtained by subtracting the measured value of the control experiment where the physiological saline solution was used instead of the lysis solution from the above measured value.

TABLE 5

| Reaction solution (μL) | Number of micro-organisms (CFU/mL) | Example 3 (C/H) | | Comparative Example 3 (H/H) | |
|---|---|---|---|---|---|
| | | 3-1 (2HCP) | 3-2 (1HCP) | 3-1 (2HCP) | 3-2 (1HCP) |
| 50 | $5 \times 10^4$ | 0.916 | 0.553 | 0.436 | 0.211 |
| 100 | $5 \times 10^4$ | 1.011 | 0.700 | 0.528 | 0.253 |

As shown in Table 5, the measured values under the C/H condition using both 1HCP and 2HCP were higher than those under the H/H condition. The measured values using 1HCP of the usual hybridization was increased when the volume of the reaction solution was increased from 50 μL to 100 μL. From these results, it was confirmed that the reaction temperature in the solution was formed in a more stepped state under the C/H condition, so that the self-assembly substance was more easily formed on the target gene and at the same time the hybridization efficiency of the usual single-stranded probes not using the PALSAR method was improved.

Example 4 and Comparative Example 4

Example 4 shows the result of the case where a partial reaction temperature region was formed in the reaction solution of the hybridization reaction using the labeled oligo-nucleotide DNA in comparison with the result of the control case where a reaction solution with a uniform reaction temperature was used (Comparative Example 4).

<Method of Preparation of Each Solution>

(1) Preparation of the Hybridization Probe Solution A

The following probe B was added to the hybridization solution-2 [4×SSC, 0.2% SDS, 1% Blocking reagent (made by La Roche Ltd.), 20% formamide, Salmon sperm DNA (10 μg/mL)] to the concentration of 0.025 pmol/μL to prepare the probe solution A.

```
Base sequence of the probe B
(Reference numeral 57 in FIG. 14) (SEQ ID NO: 9)
5'-K₁ region (CGACGACGACGACGACGACG)

T₅ region (AAATCGACAGCGTTTACAGCG)-3'
```

(2) Preparation of the Hybridization Probe Solution B

The following probe C the 5'-end of which was DIG labeled was dissolved in the hybridization solution-2 to the concentration of 0.025 pmol/μL to prepare the probe solution B.

```
Base sequence of the probe C
(Reference numeral 59 in FIG. 14) (SEQ ID NO: 10)
(the 5'-end labeled with DIG)
DIG-5'-T₆ region (TTATCACGTTAGCTACGGGCGC)-3'
```

(3) Preparation of the Lysis Solution

*Haemophilus influenzae* cultured for 18 hours in the chocolate agar culture medium was suspended in a physiological saline solution to prepare an undiluted solution of cultured micro-organisms. The solution was diluted by the physiological saline solution to the concentration of micro-organisms of 1×10⁷ CFU/mL. The diluted solution was subjected to bacteriolysis in accordance with the alkali-SDS method (Non-Patent Document 5) to make the lysis solution. The given number of micro-organisms was calculated from the number of viable micro-organisms obtained such that a dilution series of the diluted solutions of cultured micro-organisms was made and the diluted solutions were cultured with the chocolate agar.

Also as a control, the same reaction steps were carried out except that a physiological saline solution was used instead of the lysis solution.

<Preparation of a Microplate>

The following capture probe-3 having a sequence complementary to rRNA of *Haemophilus influenzae* was fixed on the strip well type 96 well microplate and used in Example 4 and Comparative Example 4.

```
Base sequence of the capture probe 3
(Reference numeral 58 in FIG. 14)) (SEQ ID NO: 11)
5'-T₇ region (CAGAGTTAAACCCCAACCCCC)

K₁' region (CGTCGTCGTCGTCGTCGTCG)-3'-Amino link
```

<Reaction and Detection Method>

(1) A Hybridization Reaction

Figure 14:
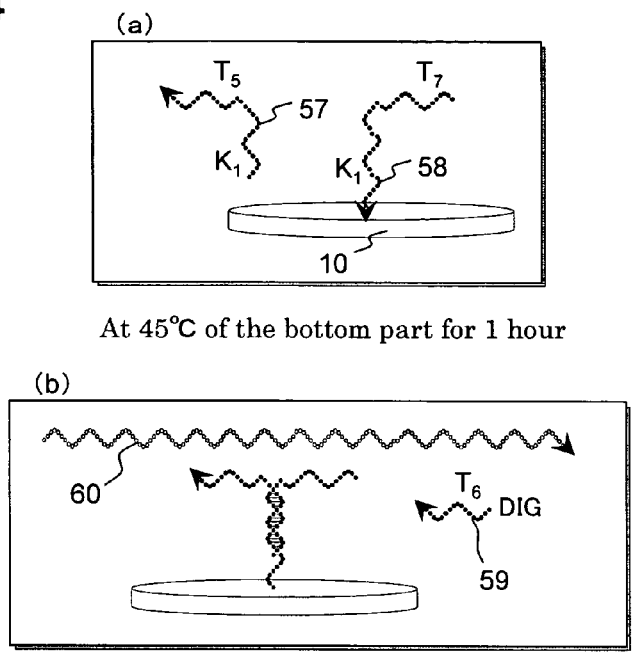
FIG. 14 is a schematic explanatory view showing a flow-chart of Example 4.

The hybridization probe solution A was divided by 50 μL each and poured into the prepared strip well type 96 well microplate, and reacted for 1 hour under the condition that the microplate temperature was set at 45° C. FIG. 14(*a*) is a schematic explanatory view of this reaction step.

After the reaction, the microplate was washed with a washer solution (50 mM-Tris, 0.3 M NaCl, 0.01%-TritonX-100, pH 7.6).

After the washing, 50 μL of the lysis solution and 50 μL of the hybridization probe solution A each was poured dividedly into the 96 well microplate from which the washing solution removed sufficiently, and sealed fixedly by a plate sealer. Incidentally, the number of micro-organisms was 4×10⁵ CFU/well.

In Example 4, the reaction was carried out for 1 hour under the condition that the bottom part of the microplate was electrically controlled at 45° C. and the top part thereof at 20° C. FIG. 14(*b*) is a schematic explanatory view of this reaction step. After the reaction, the microplate is washed by a washer solution.

On the other hand, in Comparative Example 4, the same reaction and washing were carried out in the condition that the microplate was controlled at 45° C.

(2) Detection

After the microplate wells were washed, 50 μL of POD labeled anti-digoxigenin (60 mU/mL) dissolved in 50 mM-Tris (pH 7.6) was poured thereinto, and the reaction was carried out using an incubator set at 37° C. After washing the microplate wells with a washing solution, 50 μL of a coloring solution containing a 0.2 M acetic acid buffer solution (pH 5.0), 0.06% TMB and 0.04% $H_2O_2$ was added and stood for 15 minutes in a dark place, and the absorbance thereof at 655 nm was measured. The results of the measurements are shown in Table 6 and FIG. 15.

After the microplate well is washed, 50 μL of POD labeled anti-digoxigenin

TABLE 6

| Number of micro-organisms (CFU/well) | Example 4 | Comparative Example 4 |
| --- | --- | --- |
| 0 | 0.057 | 0.056 |
| $4 \times 10^5$ | 1.433 | 0.941 |

Figure 15:
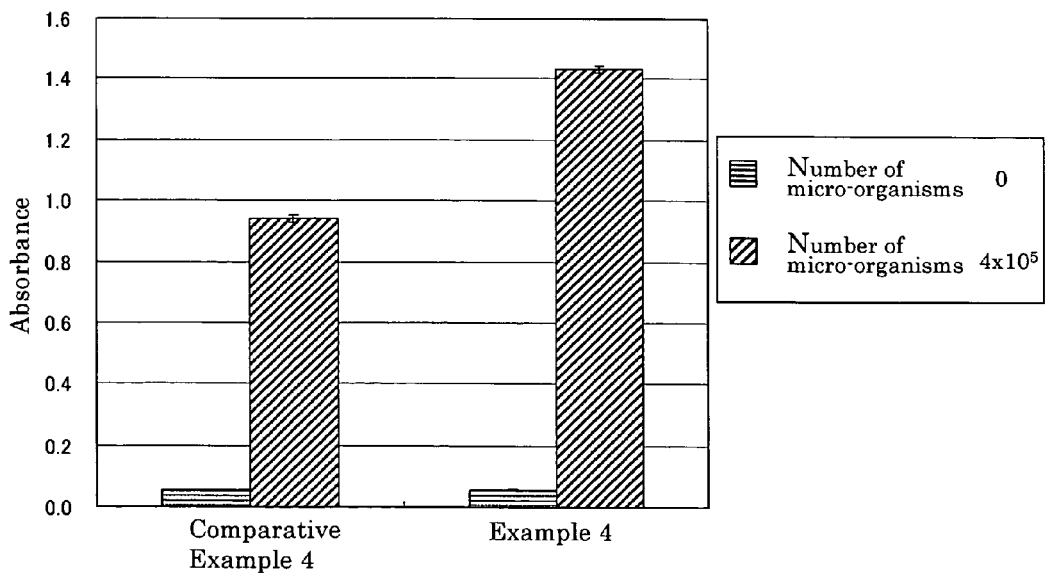
FIG. 15 is a graph showing the results of Example 4 and Comparative Example 4.

As shown in Table 6 and FIG. 15, in Example 4 wherein the bottom part of the microplate was electrically controlled at 45° C. and the top part thereof at 20° C., the measured values were higher than those of Comparative Example 4 and the detection sensitivity was improved. From these results, it was confirmed that the detection sensitivity was improved not only in the case of the signal amplification by the self-assembly reaction of the HCPs, but also in the case of using the labeled oligo-DNA.

The invention claimed is:

1. A hybridization method comprising,
performing a hybridization reaction in a reaction solution, wherein the hybridization reaction is a self-assembly reaction forming a double-stranded self-assembly substance by hybridizing plural kinds of oligonucleotide probes having complementary base sequence regions hybridizable to each other to self-assemble the oligonucleotide probes, and
wherein the reaction solution has a high temperature region and a low temperature region and the hybridization reaction preferentially occurs in the high temperature region.

2. The hybridization method according to claim 1, wherein the plural kinds of oligonucleotide probes are a pair of oligonucleotide probes consisting of a first probe and a second probe, the first probe having at least three nucleic acid regions, a nucleic acid region X, a nucleic acid region Y and a nucleic acid region Z in order from 5'-end and having the structure of the following chemical formula (1), and the second probe having at least three nucleic acid regions, a nucleic acid region X', a nucleic acid region Y' and a nucleic acid region Z' in order from 5'-end and having the structure of the following chemical formula (2)

[Chemical formula 1]

(1)

[Chemical formula 2]

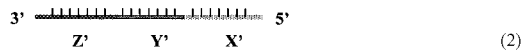

(2)

(In the above chemical formulae (1) and (2), each of X-X', Y-Y' and Z-Z' is complementary nucleic acid regions hybridizable to each other).

3. The hybridization method according to claim 1, wherein the plural kinds of oligonucleotide probes comprise:
a dimer forming probe series having n groups of plural pairs of dimer forming probes consisting of a first group to, optionally, a (2n−1)-th (n≧1) group in order, in which each of a pair of No. 1 and No. 2 oligonucleotides is divided to 3 regions of a 3'-end region, a middle region and a 5'-end region, a base sequence of the middle region of each oligonucleotide is complementary to each other, and a base sequence of the 3'-end region and a base sequence of the 5'-end region of each oligonucleotide are not complementary to each other; and
a cross-linking probe series having n groups of plural pairs of cross-linking probes consisting of a second group to, optionally, a 2n-th group in order, in which each of a pair of No. 1 and No. 2 oligonucleotides is divided to 2 regions of a 3'-end region and a 5'-end region, and a base sequence of the 3'-end region and a base sequence of the 5'-end region of each oligonucleotide are not complementary to each other; and
wherein the base sequence of the cross-linking probe is cross-linkable with plural pairs of dimers formed from the dimer forming probes.

4. The hybridization method according to claim 3, wherein in the case of n=1 each of the following pairs of the base sequences of the probes is complementary to each other: the 3'-end region of No. 1 oligonucleotide of the first group and the 3'-end region of No. 1oligonucleotide of the second group, the 5'-end region of No. 2 oligonucleotide of the first group and the 5'-end region of No. 2oligonucleotide of the second group, the 3'-end region of No. 2 oligonucleotide of the second group and the 3'-end region of No. 2oligonucleotide of the first group, and the 5'-end region of No. 1 oligonucleotide of the second group and the 5'-end region of No. 1oligonucleotide of the first group.

5. The hybridization method according to claim 4, wherein in the case of n =1 each of the following pairs of the base sequences of the probes is complementary to each other: the 3'-end region of No. 1 oligonucleotide of the first group and the 3'-end region of No. 1oligonucleotide of the second group, the 5'-end region of No. 2 oligonucleotide of the first group and the 5'-end region of No. 1oligonucleotide of the second group, the 3'-end region of No. 2 oligonucleotide of the first group and the 3'-end region of No. 2 oligonucleotide of the second group, and the 5'-end region of No. 1 oligonucleotide of the first group and the 5'-end region of No. 2 oligonucleotide of the second group.

6. The hybridization method according to claim 3, wherein in the case of n≧2 each of the following pairs of the base sequences of the probes is complementary to each other: the 3'-end region of No. 1 oligonucleotide of the (2n−3)-th group and the 3'-end region of No. 1-oligonucleotide of the (2n−2)-th group, the 5'-end region of No. 2 oligonucleotide of the (2n−3)-th group and the 5'-end region of No. 2-oligonucleotide of the (2n−2)-th group, the 3'-end region of No. 2 oligonucleotide of the (2n−2)-th group and the 3'-end region of No. 2-oligonucleotide of the (2n−1)-th group, the 5'-end region of No. 1 oligonucleotide of the (2n−2)-th group and the 5'-end region of No. 1-oligonucleotide of the (2n−1)-th group, the 3'-end region of No. 1 oligonucleotide of the last group of the dimer forming probe series and 3'-end region of No. 1 oligonucleotide of the last group of the cross-linking probe series, the 5'-end region of No. 2 oligonucleotide of the last group of the dimer forming probe series and the 5'-end region of No. 2 oligonucleotide of the last group of the cross-linking probe series, the 3'-end region of No. 2 oligonucleotide of the last group of the cross-linking probe series and the 3'-end region of No. 2 oligonucleotide of the first group of the dimer forming probe series, and the 5'-end region of No. 1 oligonucleotide of the last group of the cross-linking probe series and the 5'-end region of No. 1 oligonucleotide of the first group of the dimer forming probe series.

7. The hybridization method according to claim 3, wherein in the case of n≧2 each of the following pairs of the base sequences of the probes is complementary to each other: the 3'-end region of No. 1-oligonucleotide of the (2n−3)-th group and the 3'-end region of No. 1oligonucleotide of the (2n−2)-th group, the 5'-end region of No. 2 oligonucleotide of the (2n−3)-th group and the 5'-end region of No. 2oligonucleotide of the (2n−2)-th group, the 3'-end region of No. 2 oligonucleotide of the (2n−2)-th group and the 3'-end region of No. 2oligonucleotide of the (2n−1)-th group, the 5'-end region of No. 1 oligonucleotide of the (2n−2)-th group and the 5'-end region of No. 1oligonucleotide of the (2n−1)-th group, the 3'-end region of No. 1 oligonucleotide of the last group of the dimer forming probe series and the 3'-end region of No. 1 oligonucleotide of the last group of the cross-linking probe series, the 5'-end region of No. 2 oligonucleotide of the last group of the dimer forming probe series and the 5'-end region of No. 1 oligonucleotide of the last group of the cross-linking probe series, the 3'-end region of No. 2 oligonucleotide of the last group of the cross-linking probe series and the 3'-end region of No. 2 oligonucleotide of the first group of the dimer forming probe series, and the 5'-end region of No. 2-oligonucleotide of the last group of the cross-linking probe series and the 5'-end region of No. 1 oligonucleotide of the first group of the dimer forming probe series.

8. The hybridization method according to claim 1, wherein the plural kinds of oligonucleotide probes comprise:
plural pairs of dimer forming probes having plural groups of dimer forming probes consisting of a first group to a k-th (k≧2) group in order, in which each of a pair of No. 1 and No. 2 oligonucleotides is divided to 3 regions of a 3'-end region, a middle region and a 5'-end region, a base sequence of the middle region of each oligonucleotide is complementary to each other, and a base sequence of the 3'-end region and a base sequence of the 5'-end region of each oligonucleotide are not complementary to each other; and
wherein each of the following pairs of the base sequences of the probes is complementary to each other:
(a) the 3'-end region of No. 1 oligonucleotide of the (k−1)-th group and the 3'-end region of No. 2 oligonucleotide of the k-th group,
(b) the 5'-end region of No. 2 oligonucleotide of the (k−1)-th group and the 5'-end region of No. 1 oligonucleotide of the k-th group,
(c) the 3'-end region of No. 1 oligonucleotide of the last group and the 3'-end region of No. 2oligonucleotide of the first group,
(d) the 5'-end region of No. 2 oligonucleotide of the last group and the 5'-end region of No. 1oligonucleotide of the first group.

9. The hybridization method according to claim 1, wherein the plural kinds of oligonucleotide probes comprise:
plural pairs of dimer forming probes having plural groups of dimer forming probes consisting of a first group to a k-th (k≧2) group in order, in which each of a pair of No. 1 and No. 2 oligonucleotides is divided to 3 regions of a 3'-end region, a middle region and a 5'-end region, a base sequence of the middle region of each oligonucleotide is complementary to each other, and a base sequence of the 3'-end region and a base sequence of the 5'-end region of each oligonucleotide are not complementary to each other; and wherein each of the following pairs of the base sequences of the probes is complementary to each other: and
wherein each of the following pairs of the base sequences of the probes is complementary to each other:
(a) the 3'-end region of No. 1-oligonucleotide of the (k−1)-th group and the 3'-end region of No. 2-oligonucleotide of the k-th group,
(b) the 5'-end region of No. 1-oligonucleotide of the (k−1)-th group and the 5'-end region of No. 2-oligonucleotide of the k-th group,
(c) the 3'-end region of No. 1-oligonucleotide of the last group and the 3'-end region of No. 2-oligonucleotide of the first group,
(d) the 5'-end region of No. 1-oligonucleotide of the last group and the 5'-end region of No. 2-oligonucleotide of the first group.

10. The hybridization method according to claim 1, wherein the oligonucleotide comprises at least one kind of nucleotide selected from the group consisting of DNA, RNA, PNA and LNA.

11. The hybridization method according to claim 1, wherein at least one of the oligonucleotide is labeled with a labeling substance.

12. The hybridization method according to claim 1, wherein the labeling substance is a radioisotope, a fluorescent substance, a luminous substance, a coloring substance, a coloring enzyme or a luminous enzyme.

13. A signal amplifying method, wherein the detection sensitivity of a target gene in a reaction device for detecting a gene is improved using a self-assembly reaction forming a double-stranded self-assembly substance by hybridizing plural kinds of oligonucleotide probes having complementary base sequence regions hybridizable to each other to self-assemble the oligonucleotides, and wherein the self-assembly reaction is performed using the hybridization method according to claim 1.

14. The signal amplifying method according to claim 13, wherein the reaction device is a microplate, a DNA microarray or a magnetic particle.

15. The signal amplifying method according to claim 13, wherein the target gene is single-stranded DNA and/or RNA.

16. The signal amplifying method according to claim 13, wherein the target gene is double-stranded DNA and/or RNA.

17. The signal amplifying method according to claim 13, wherein the target gene includes SNPs (Single Nucleotide Polymorphisms).

18. The signal amplifying method according to claim 13, wherein at least one of the oligonucleotide probes to be used for the self-assembly reaction has a complementary base sequence at a part of the target gene.

19. The signal amplifying method according to claim 13, wherein there is used an assist probe having a region complementary to each base sequence of the target gene and the oligonucleotide probe to bind the target gene to the oligonucleotide probe.

20. The signal amplifying method according to claim 13, wherein the oligonucleotide probe comprises at least one kind of polynucleotide selected from the group consisting of DNA, RNA, PNA and LNA.

21. The signal amplifying method according to claim 13, wherein at least one of the oligonucleotide probe is labeled with a labeling substance.

22. The signal amplifying method according to claim 21, wherein the labeling substance is a radioisotope, a fluorescent substance, a luminous substance, a coloring substance, a coloring enzyme or a luminous enzyme.

23. The signal amplifying method according to claim 13, wherein a labeled probe is hybridized to the self-assembly substance bound to the target gene to detect the presence of the self-assembly substance.

24. The signal amplifying method according to claim 23, wherein the labeled probe is labeled with a coloring enzyme, a luminous enzyme or a radioisotope.

25. The signal amplifying method according to claim 13, wherein a fluorescent substance bindable to a nucleic acid is added to the self-assembly substance and the presence of the self-assembly substance is detected by a photochemical change of the fluorescent substance.

26. A method for detecting a target gene, the method comprising the use of the signal amplifying method according to claim 13.

27. A method for detecting a target gene, the method comprising the use of a hybridization reaction of oligonucleotides in a reaction solution to detect a gene, wherein the hybridization reaction includes a hybridization reaction carried out using the hybridization method according to claim 1 in a reaction device.

28. The method for detecting a target gene according to claim 27, wherein the reaction device for detecting a gene is a microplate, a DNA microarray or an magnetic particle.

29. The method for detecting a target gene according to claim 27, wherein at least one of the oligonucleotides to be used for the hybridization reaction has a complementary base sequence to a part of the target gene.

30. The method for detecting a target gene according to claim 27, wherein the target gene is single-stranded DNA and/or RNA.

31. The method for detecting a target gene according to claim 27, wherein the target gene is double-stranded DNA and/or RNA.

32. The method for detecting a target gene according to claim 27, wherein the target gene has SNPs (Single Nucleotide Polymorphisms).

* * * * *

SEQUENCE LISTING

```
<160> NUMBER OF SEQ ID NOS: 11

<210> SEQ ID NO 1
<211> LENGTH: 60
<212> TYPE: DNA
<213> ORGANISM: Artificial
<220> FEATURE:
<223> OTHER INFORMATION: synthetic

<400> SEQUENCE: 1
catgtctcgt gtcttgcatc ctgctacagt gaacaccatc gttctcgaca tagaccagtc        60

<210> SEQ ID NO 2
<211> LENGTH: 60
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Digoxigenin attached at the 5' end

<400> SEQUENCE: 2
gatgcaagac acgagacatg gatggtgttc actgtagcag gactggtcta tgtcgagaac        60

<210> SEQ ID NO 3
<211> LENGTH: 101
<212> TYPE: DNA
<213> ORGANISM: Artificial
<220> FEATURE:
<223> OTHER INFORMATION: synthetic

<400> SEQUENCE: 3
tagctaatgc agcgcggatc cgagaaagtt catagatata ccatgtctcg tgtcttgcat        60
cctgctacag tgaacaccat cgttctcgac atagaccagt c                           101

<210> SEQ ID NO 4
<211> LENGTH: 101
<212> TYPE: DNA
<213> ORGANISM: Artificial
<220> FEATURE:
<223> OTHER INFORMATION: synthetic
```

-continued

```
<400> SEQUENCE: 4
catgtctcgt gtcttgcatc ctgctacagt gaacaccatc gttctcgaca tagaccagtc    60
gtatatctat gaactttctc atctataagt gacagcaaga c                       101

<210> SEQ ID NO 5
<211> LENGTH: 41
<212> TYPE: DNA
<213> ORGANISM: Artificial
<220> FEATURE:
<223> OTHER INFORMATION: synthetic

<400> SEQUENCE: 5
cgacgacgac gacgacgacg gcggttcaaa atattatccg g                        41

<210> SEQ ID NO 6
<211> LENGTH: 41
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (41)..(41)
<223> OTHER INFORMATION: Aminolink attached at the 3' end

<400> SEQUENCE: 6
cgtctttcac ttttgaacca tcgtcgtcgt cgtcgtcgtc g                        41

<210> SEQ ID NO 7
<211> LENGTH: 81
<212> TYPE: DNA
<213> ORGANISM: Artificial
<220> FEATURE:
<223> OTHER INFORMATION: synthetic

<400> SEQUENCE: 7
catgtctcgt gtcttgcatc ctgctacagt gaacaccatc gttctcgaca tagaccagtc    60
atctataagt gacagcaaga c                                              81

<210> SEQ ID NO 8
<211> LENGTH: 21
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Aminolink attached at the 3' end

<400> SEQUENCE: 8
cgtctttcac ttttgaacca t                                              21

<210> SEQ ID NO 9
<211> LENGTH: 41
<212> TYPE: DNA
<213> ORGANISM: Artificial
<220> FEATURE:
<223> OTHER INFORMATION: synthetic

<400> SEQUENCE: 9
cgacgacgac gacgacgacg aaatcgacag cgtttacagc g                        41

<210> SEQ ID NO 10
<211> LENGTH: 22
```

-continued

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Digoxigenin attached at the 5' end

<400> SEQUENCE: 10
ttatcacgtt agctacgggc gc                                         22

<210> SEQ ID NO 11
<211> LENGTH: 41
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (41)..(41)
<223> OTHER INFORMATION: Aminolink attached at the 3' end

<400> SEQUENCE: 11
cagagttaaa ccccaacccc ccgtcgtcgt cgtcgtcgtc g                    41
```